(12) United States Patent
Zhang et al.

(10) Patent No.: US 11,259,763 B2
(45) Date of Patent: Mar. 1, 2022

(54) SCAN GANTRY FOR MEDICAL IMAGING SYSTEM

(71) Applicant: General Electric Company, Schenectady, NY (US)

(72) Inventors: Xiaoyan Zhang, Beijing (CN); Xuyong Yang, Beijing (CN); Jun Guo, Beijing (CN)

(73) Assignee: General Electric Company, Schenectady, NY (US)

( * ) Notice: Subject to any disclaimer, the term of this patent is extended or adjusted under 35 U.S.C. 154(b) by 128 days.

(21) Appl. No.: 16/716,964

(22) Filed: Dec. 17, 2019

(65) Prior Publication Data
US 2020/0205757 A1   Jul. 2, 2020

(30) Foreign Application Priority Data
Dec. 29, 2018  (CN) .......................... 201811633885.3

(51) Int. Cl.
*A61B 6/00* (2006.01)
*A61B 6/03* (2006.01)
*A61B 6/10* (2006.01)

(52) U.S. Cl.
CPC ............ *A61B 6/4447* (2013.01); *A61B 6/032* (2013.01); *A61B 6/105* (2013.01)

(58) Field of Classification Search
CPC ....... A61B 6/4447; A61B 6/032; A61B 6/105; A61B 6/035; A61B 6/4435
USPC .......................................................... 378/17
See application file for complete search history.

(56) References Cited

U.S. PATENT DOCUMENTS

| | | | | |
|---|---|---|---|---|
| 5,097,497 A | * | 3/1992 | Deucher | A61B 6/4405 378/196 |
| 7,658,540 B2 | * | 2/2010 | Jensen | A61B 6/4441 378/197 |
| 7,975,358 B2 | * | 7/2011 | Campbell | A61B 6/4435 29/434 |
| 8,128,286 B2 | * | 3/2012 | Shindo | A61B 6/035 378/197 |
| 8,191,222 B2 | * | 6/2012 | Campbell | A61B 6/4435 29/434 |
| 8,667,655 B2 | * | 3/2014 | Campbell | A61B 6/037 29/243.5 |
| 8,807,833 B2 | * | 8/2014 | Sharpless | G01M 1/36 378/197 |
| 9,522,286 B2 | * | 12/2016 | Bergfjord | A61N 5/01 |
| 10,029,123 B2 | * | 7/2018 | Bergfjord | A61N 5/01 |
| 10,076,294 B2 | * | 9/2018 | Basu | F16C 19/507 |

(Continued)

*Primary Examiner* — David P Porta
*Assistant Examiner* — Gisselle M Gutierrez

(57) ABSTRACT

The present invention provides a scan gantry for a medical imaging system. The scan gantry comprises a bottom supporting frame and a tilt supporting frame that are connected to each other, wherein the tilt supporting frame is tiltable relative to the bottom supporting frame. The scan gantry further comprises a locking mechanism connected between the bottom supporting frame and the tilt supporting frame. In the process that the tilt supporting frame is being tilted relative to the bottom supporting frame, the locking mechanism is in an unlocked state; and when the tilt supporting frame is stationary relative to the bottom supporting frame, the locking mechanism is in a locked state to prevent the tilt supporting frame from moving relative to the bottom supporting frame.

1 Claim, 30 Drawing Sheets

(56) References Cited

U.S. PATENT DOCUMENTS

| | | | |
|---|---|---|---|
| 2002/0168044 A1* | 11/2002 | Tybinkowski | A61B 6/4447 378/4 |
| 2008/0192885 A1* | 8/2008 | Teofilovic | A61B 6/10 378/4 |
| 2014/0205059 A1* | 7/2014 | Sharpless | A61B 6/4429 378/17 |
| 2014/0275953 A1* | 9/2014 | Gregerson | A61B 6/4405 600/407 |
| 2018/0078223 A1* | 3/2018 | Oishi | A61B 6/0487 |
| 2020/0205757 A1* | 7/2020 | Zhang | A61B 6/4447 |
| 2021/0022691 A1* | 1/2021 | Gregerson | A61B 6/4405 |

\* cited by examiner

SCAN GANTRY FOR MEDICAL IMAGING SYSTEM

TECHNICAL FIELD

The present invention relates to the field of medical imaging, and in particular, to a scan gantry for a medical imaging system.

BACKGROUND

A scan gantry can be found in medical imaging systems such as computed tomography (CT) systems. The scan gantry generally includes a base and a rotatable member disposed on the base. The rotatable member is provided with imaging components such as an X-ray tube and a detector. These components are driven to rotate at a high speed so as to implement three-dimensional imaging on a subject in a scanning cavity in the middle of the rotatable member.

With the continuous development of imaging technology, the rotatable member further needs to be tiltable in some usage occasions. For example, when one intends to adjust specific imaging angles and/or lower the dose of ray applied to a subject, the rotatable member needs to be tilted as it rotates at a high speed to implement the imaging process. At present, scan gantries having a tilting function are inhibited from further increase in the rotational speed due to the vibration amplitude of the rotating member during rotation. A higher rotational speed would help diagnose more diseases and reduce the dose of X-rays absorbed by patients.

SUMMARY

An objective of the present invention is to provide a novel scan gantry for a medical imaging system, such that when a rotating member rotates on a scan gantry having a tilting function, the vibration value would be lower and more stable, thereby achieving better image quality. Alternatively, holding the image quality constant, the present invention enables the rotating member to rotate faster on a scan gantry having a tilting function.

An exemplary embodiment of the present invention provides a scan gantry for a medical imaging system. The scan gantry comprises a bottom supporting frame and a tilt supporting frame that are connected to each other, wherein the tilt supporting frame is tiltable relative to the bottom supporting frame. The scan gantry further comprises a locking mechanism connected between the bottom supporting frame and the tilt supporting frame. In the process of tilting the tilt supporting frame relative to the bottom supporting frame, the locking mechanism is in an unlocked state; and when the tilt supporting frame is stationary relative to the bottom supporting frame, the locking mechanism is in a locked state to prevent the tilt supporting frame from moving relative to the bottom supporting frame.

Other features and aspects will become clear through the following detailed description, accompanying drawings, and claims.

BRIEF DESCRIPTION OF THE DRAWINGS

A description of exemplary embodiments of the present invention with reference to accompanying drawings will help those skilled in the art better understand the present invention. In the drawings.

DETAILED DESCRIPTION OF THE EMBODIMENTS

Specific implementations of the present invention will be described in the following. It should be noted that during the specific description of the implementations, it is impossible to describe all features of the actual implementations in detail in this description for the sake of brief description. It should be understood that in the actual implementation of any of the implementations, as in any engineering project processes or design project processes, a variety of specific decisions are often made in order to achieve the developer's specific objectives and meet system-related or business-related restrictions, which will vary from one implementation manner to another. It should also be understood that although such efforts made during such development processes may be complex and lengthy, changes in design, manufacturing, production or the like based on the technical content disclosed in this disclosure are only conventional technical means for those of ordinary skill in the art related to content disclosed in the present invention. It should not be construed as that the content of this disclosure is insufficient.

Unless otherwise defined, the technical or scientific terms used in the claims and the description are as they are usually understood by those of ordinary skill in the art to which the present invention pertains. The words "first," "second" and similar words used in the description and claims of the patent application of the present invention do not denote any order, quantity or importance, but are merely intended to distinguish between different constituents. The word "one," "a/an" or a similar word is not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Figure 1:
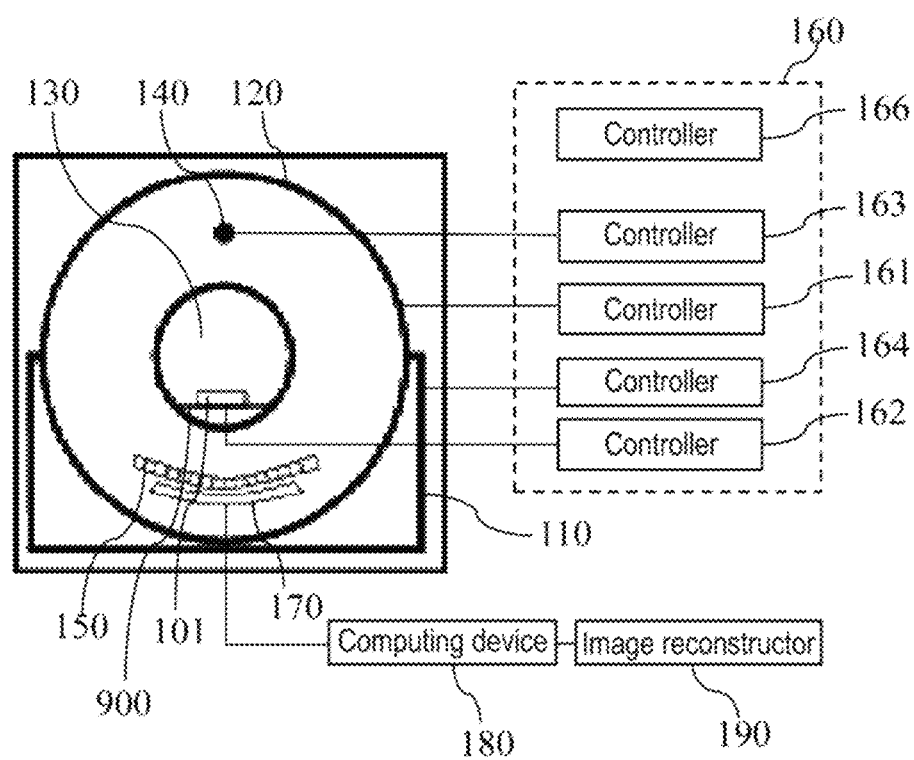
FIG. 1 is a schematic structural view of a medical imaging system in an embodiment.

FIG. 1 is a schematic structural view of a medical imaging system in an embodiment. As an example, the medical imaging system is a computed tomography (CT) system. As shown in FIG. 1, the medical imaging system includes a scan gantry. The scan gantry includes a supporting part 110 and a rotating part 120. The rotating part 120 is provided with a scanning cavity 130, the scanning cavity being used for accommodating a subject 101 to be imaged. In an embodiment, a to-be-imaged part of the subject 101 may be positioned in the scanning cavity 130 through a movable examining table 900. The rotating part 120 is provided with an X-ray source 140 and a detector 150. The X-ray source 140 and the detector 150 are oppositely disposed on two sides of the scanning cavity 130. The x-ray source 140 is used for projecting an X-ray beam. The X-ray beam penetrates the subject 101 and then turns into an attenuated X-ray beam. In an embodiment, the detector 150 receives the attenuated X-ray beam and converts it into analog image data.

In an embodiment, the rotating part 120 may rotate at a high speed so that the X-ray source 140 projects X-ray beams at a plurality of angles, such that generated image data has different viewing angles.

In an embodiment, the rotating part 120 may further be disposed in a tilted manner to meet specific imaging needs, for example, to achieve a smaller ray dose or an optimal ray incidence angle of the subject 101. In an example, the supporting part 110 of the scan gantry may include a tiltable portion. The rotating part 120 is configured to be capable of being tilted together with the tiltable portion. For example, the rotating part 120 may be tilted so that the central axis of the scanning cavity 130 forms an angle with the horizontal direction.

The medical imaging system may further include a control mechanism 160. The control mechanism 160 includes, for example, a controller 161 for controlling the rotational speed/rotational position of the rotating part 120, which may be specifically used for controlling the working state of a motor of the rotating part 120. The control mechanism 160 may further include a controller 162 for controlling the movement/lifting of the examining table 300, a controller 163 for controlling the working state of the x-ray source 110, and a controller 164 for controlling the tiltable portion of the supporting part 110 and the tilting of the rotating part 120. Further, the control mechanism 160 may further include a controller 166 for controlling the locking and unlocking of the tiltable portion of the supporting part 110. The aforementioned controllers may be integrated together or separately disposed, and the various controls described above may be implemented in response to operating instructions that the operator enters via an operating console.

The medical imaging system may further include a data acquisition system 170 for sampling and digitizing the analog image data.

The medical imaging system may further include a computing device 180 for processing the image data that is sampled and digitized by the data acquisition system 170. In an example, the computing device 180 stores the image data in a storage device, such as a mass memory. The mass memory may include a hard disk drive, a floppy disk drive, a CD-read/write (CD-R/W) drive, a digital versatile disc (DVD) drive, a flash drive, and/or a solid-state storage device.

In addition, the computing device 180 is further used for providing instructions and parameters to the data acquisition system 170 and some or all of the controllers of the control mechanism 160 to control system operations, such as data acquisition and/or processing.

The medical imaging system may further include an image reconstructor 190, which reconstructs an image of the to-be-imaged part of the subject 101 based on the digitized image data using an appropriate image reconstruction method. Although the image reconstructor 190 is illustrated as a separate entity in FIG. 1, in some embodiments, the image reconstructor 190 may form part of the computing device 180.

Scan Gantry in First Embodiment

Figure 2:
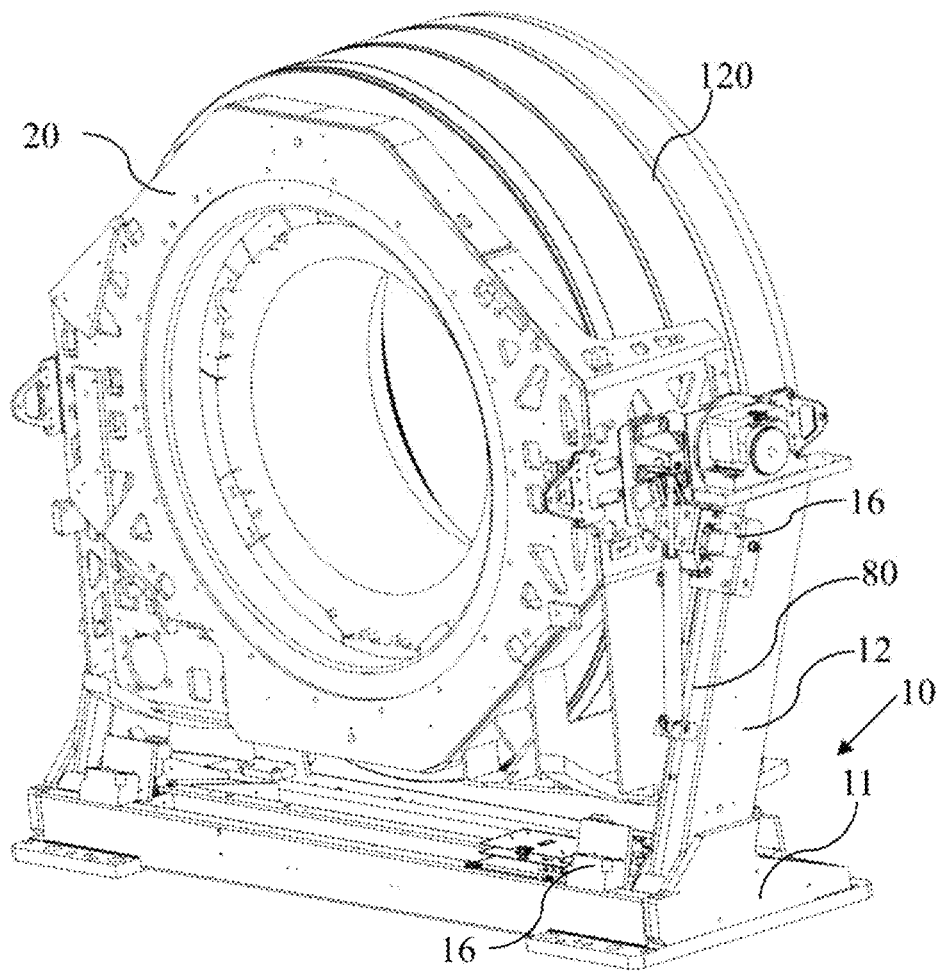
FIG. 2 and FIG. 3 illustrate a scan gantry for a medical imaging system in a first embodiment of the present invention.
Figure 3:
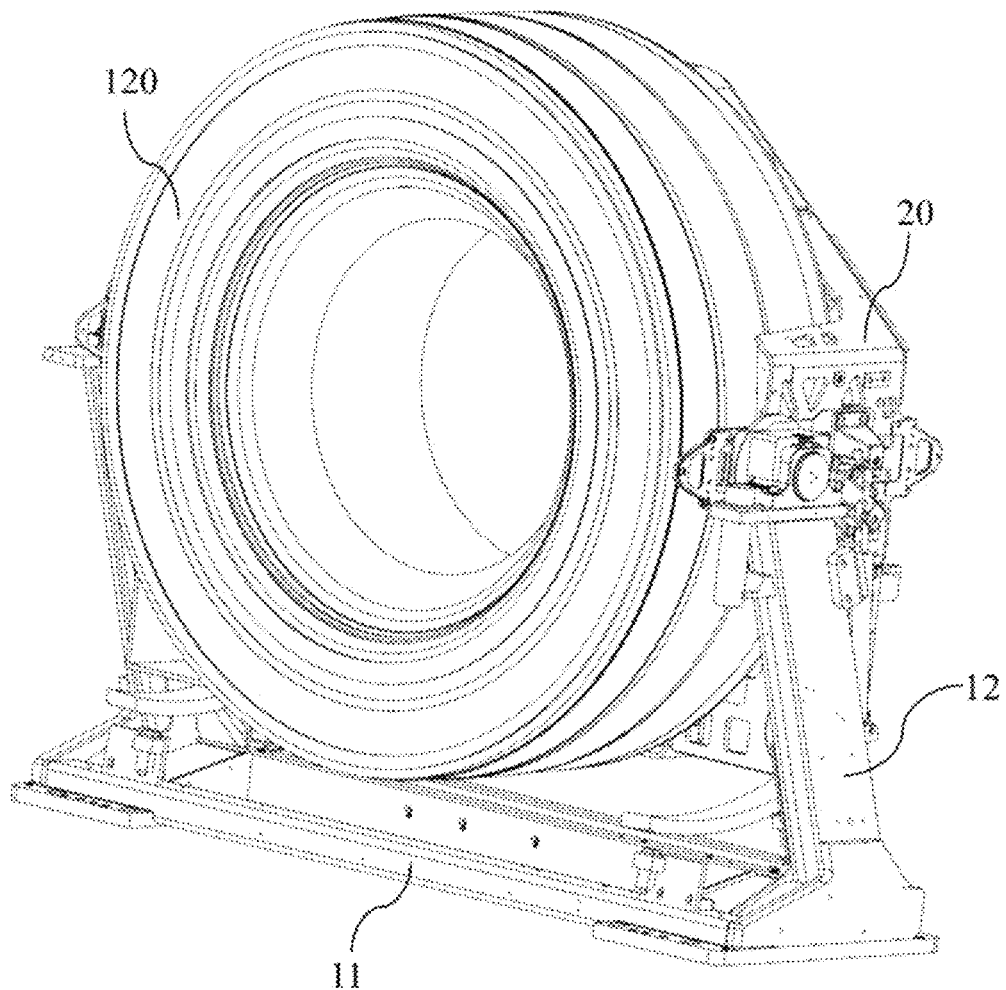

FIG. 2 and FIG. 3 illustrate a scan gantry for a medical imaging system in a first embodiment of the present invention. As shown in FIG. 2 and FIG. 3, the scan gantry includes a bottom supporting frame 10 and a tilt supporting frame 20 that are connected to each other. Like the tiltable portion of the supporting part 110 described above, the tilt supporting frame 20 can be tilted relative to the bottom supporting frame 10, and the rotating part 120 of the medical imaging system is attached to the tilt supporting frame 20 and can be tilted together with the tilt supporting frame 20.

In an embodiment, the bottom supporting frame 10 includes a base 11 and two opposite side portions 12 connected to the base 11. Two ends of the tilt supporting frame 20 may be respectively pivotally connected to the two side portions 12 of the bottom supporting frame 10 and suspended relative to the base. In this way, the tilt supporting frame 20 can be tilted and rotated relative to the bottom supporting frame 10.

In a usage scenario, the rotating part 120 needs to rotate in a tilted state. At this time, the tilt supporting frame 20 is controlled to tilt at a certain angle to a required position; and then, the tilt supporting frame 20 is locked at this position. Afterwards, the rotating part 120 can be controlled to rotate. If the rotating part needs to recover to the initial position (e.g. the central axis of the scanning cavity is parallel to the horizontal direction), then the rotating part 120 is first controlled to stop rotating, the tilt supporting frame 20 is unlocked, and then the tilt supporting frame 20 is reversely rotated back to the initial position.

In an existing embodiment, the bottom supporting frame 10 and the tilt supporting frame 20 may be connected by means of a rotating shaft, and the tilt supporting frame 20 is driven to tilt to a required angle by means of extension or retraction of a telescopic rod 80 that is connected between the bottom supporting frame 10 and the tilt supporting frame 20. The telescopic rod described herein may be a telescopic hydraulic cylinder, an electric push rod, or other members having a telescopic function. The telescopic rod 80 can only extend or retract in response to a change of the relative position between the bottom supporting frame 10 and the tilt supporting frame 10. After the tilting stops, the telescopic rod 80 can provide a certain supporting effect. Since the tilt supporting frame 20 cannot be completely locked relative to the bottom supporting frame 10, the rotating part 120 still obviously vibrates during high-speed rotation.

The scan gantry in this embodiment of the present invention further includes a locking mechanism 16 connected between the bottom supporting frame 10 and the tilt supporting frame 20. In the process that the tilt supporting frame 20 is being tilted relative to the bottom supporting frame 10, the locking mechanism is in an unlocked state; and when the tilt supporting frame 20 is stationary relative to the bottom supporting frame 10, the locking mechanism is in a locked state to prevent the tilt supporting frame from moving relative to the bottom supporting frame. The locking mechanism is used for adding a fixing point that can be locked or unlocked between the bottom supporting frame 10 and the tilt supporting frame 20. The tilt supporting frame 20 can stop at any position within a certain tilting range and be locked by the locking mechanism and be stationary. When locked, the locking mechanism adds a fixing point between the bottom supporting frame and the tilt supporting frame so that the scan gantry has higher stability.

One or a plurality of locking mechanisms 16 may exist. For example, to achieve locking stability, a plurality of locking mechanisms 16 may be disposed at different positions of the bottom supporting frame 10 and the tilt supporting frame 20.

Figure 4:
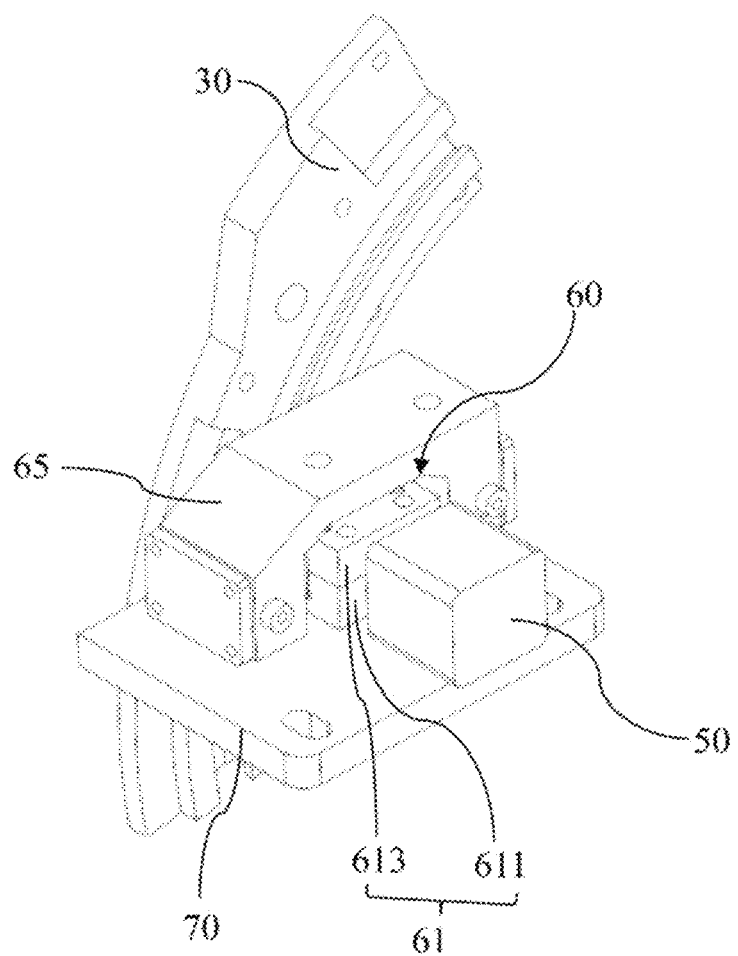
FIG. 4 illustrates a locking mechanism of the scan gantry in FIG. 2.

FIG. 4 illustrates the locking mechanism 16 of the scan gantry in this embodiment of the present invention, which includes a locking part 30, an engaging part 40, and a driving part 50.

With reference to FIG. 2 to FIG. 4, the locking part 30 is disposed on the tilt supporting frame 20 according to a tilt trajectory of the tilt supporting frame 20 and can move synchronously with the tilt supporting frame 20. Specifically, the effective size (for example, length, angle, and area) of the locking part 30 is related to the maximum tilting range of the tilt supporting frame 20. For example, when the tilt supporting frame 20 is being tilted at the maximum angle, the locking part 30 has a large enough size to lock the tilt supporting frame 20. More specifically, the shape of the effective portion of the locking part 30 is related to the moving trajectory of the tilt supporting frame 20. For example, the effective portion of the locking part 30 forms an arc shape with a radian matching the radian of the tilt trajectory of the tilt supporting frame 20, so that the locking part 30 can lock the tilt supporting frame 20 when the tilt supporting frame 20 is at any position within the tilting range thereof. For example, the tilt trajectory of the tilt supporting frame 20 is a segment of circular arc. The locking part 30 is disposed on the tilt supporting frame 20 according to the tilt trajectory and extends to form another segment of circular arc concentric with the aforementioned segment of circular arc.

The engaging part 40 is disposed on the bottom supporting frame 10 and used for engaging with the locking part 30 and locking the tilt supporting frame 20 relative to the bottom supporting frame 10 when moved from an initial unlocked position to a locked position, or used for unlocking the locking part 30 from the tilt supporting frame 20 when returning from the locked position to the initial position. The locking and unlocking may be implemented when the tilt supporting frame 20 is tilted at any position.

The driver 50 is used for driving the engaging part 40 to move to the locked position or return to the initial unlocked position.

In this embodiment, the engaging part 40 and the driving part 50 may both be mounted on the bottom supporting frame 10 by means of a fixing plate 70. For example, the fixing plate 70 is fixed to the bottom supporting frame 10 by means of screws or other mounting methods and carries thereon the engaging part 40 and the driving part 50.

The structure, connection mode, and working principles of the locking part 30, the engaging part 40, and the driving part 50 are further described below with reference to the accompanying drawings.

Figure 5:
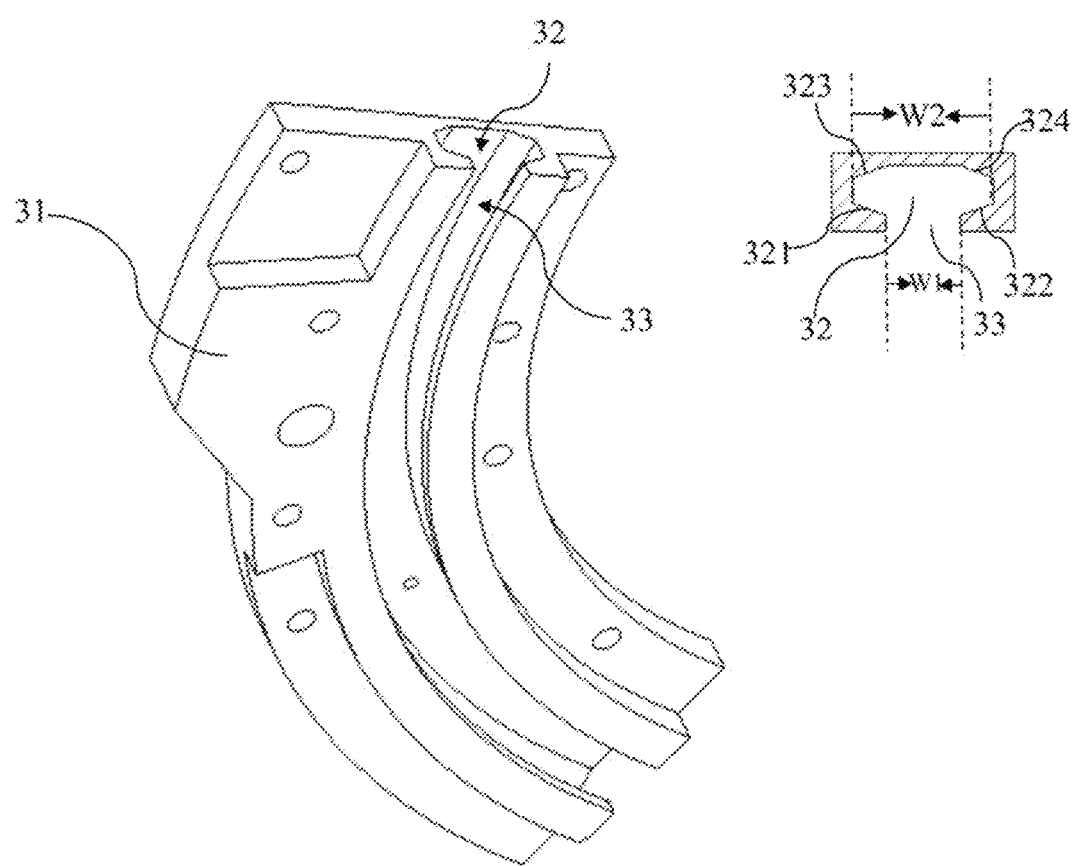
FIG. 5 is a schematic structural view of a locking part in FIG. 4.

FIG. 5 is a schematic structural view of the locking part 30 in FIG. 4. With reference to FIG. 5, the locking part 30 includes a body 31, and a slot 32 extending into an arc shape is formed on the body 31. In an implementation manner, the body 31 may be made of a rigid material and is fixedly mounted on the tilt supporting frame 20 by means of screws or other mounting members. In other embodiments, the tilt supporting frame 20 itself may serve as the body of the locking part 30. That is, the slot 32 may be provided on the tilt supporting frame 20 according to the actual situation. FIG. 5 further schematically illustrates a cross-sectional view of the slot 32 of the locking part 30, where the shape of the slot 32 is illustrated. The slot 32 may be used, in combination with the engaging part disposed on the tilt supporting frame 20, for locking the tilt supporting frame 20 relative to the bottom supporting frame 10, which will be described in detail below with reference to the specific structure of the engaging part.

Figure 6:
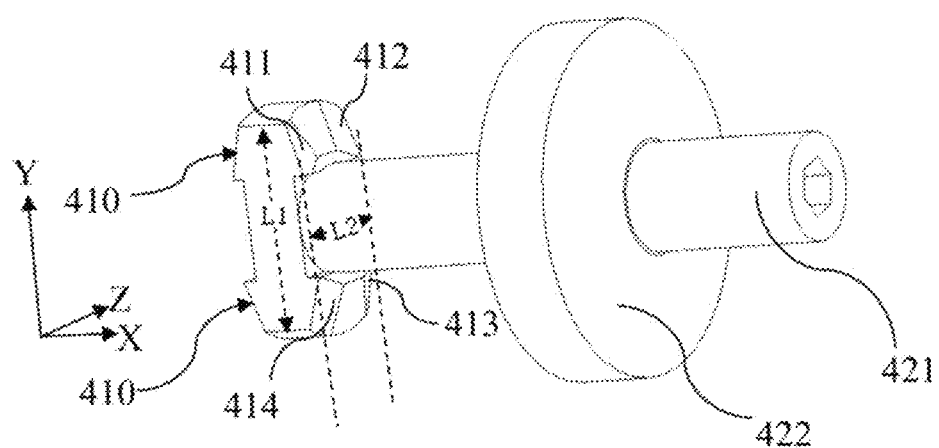
FIG. 6 and FIG. 7 schematically illustrate an engaging part in FIG. 4.
Figure 7:
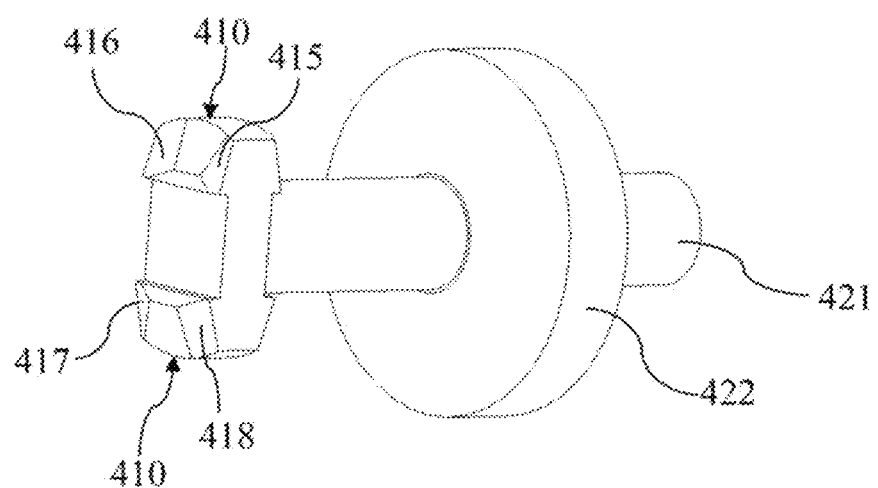

With reference to FIG. 6 and FIG. 7, FIG. 6 and FIG. 7 schematically illustrate the engaging part 40 in FIG. 4. The engaging part 40 includes a locking tongue 41 of the engaging part 40 capable of rotating from the initial position to the locked position to abut against inner walls of the slot 32.

With reference to FIG. 5 to FIG. 8, the slot 32 is in communication with the outside through an opening 33. A width W1 of the opening 33 is smaller than a width W2 of the slot 32. The locking tongue 41 is disposed in the slot 32 through the opening 33, and the locking tongue 41 has a longitudinal length L1 and a transverse length L2. The transverse length L2 of the locking tongue 41 is smaller than the width W1 of the opening so that the locking tongue 1 can be put into the slot 32, and the longitudinal length L1 of the locking tongue 41 is larger than the width W2 of the slot 32 so that the locking tongue 41 can be snapped into the slot 32 at the locked position. The longitudinal length L1 of the locking tongue 41 may further be larger than the width of the slot to further achieve locking stability. For example, in an embodiment, when the locking tongue 41 is at the initial position, the locking tongue 41 is longitudinally placed in the slot 32 (the longitudinal direction of the locking tongue 41 is roughly parallel to the extension direction of the slot 32) and forms a gap with the inner walls of the slot 32; when the locking tongue 41 is at the locked position, the locking tongue 41 is placed in the slot 32 at a certain angle (the longitudinal direction of the locking tongue 41 has a certain angle with the extension direction of the slot 32) and abuts against the inner walls of the slot 32. Further, the locking tongue 41 has two wedge ends 410 opposite to each other in the longitudinal direction thereof. Each wedge end 410 is provided with at least one pair of wedge surfaces opposite to each other in a vertical direction thereof. The vertical direction is perpendicular to the traverse direction and longitudinal direction of the locking tongue 41. The slot 32 includes at least one pair of inner walls abutting against the at least one pair of wedge surfaces.

For example, four wedge surfaces 411, 412, 413, and 414 on one side of the locking tongue 41 are marked in FIG. 6; four wedge surfaces 415, 516, 417, and 418 on the other side of the locking tongue 41 are marked in FIG. 7; the wedge end 410 on the upper end has two pairs of wedge surfaces: 411 and 415 as well as 412 and 416; the wedge end 410 on the lower end has two pairs of wedge surfaces: 413 and 417 as well as 414 and 418. An intermediate transition plane is connected between every two adjacent wedge surfaces. For the wedge body 410 on the upper end, the wedge surfaces 411, 412, 415, and 416 and four corresponding intermediate planes are connected to form an octahedron. Since at least four surfaces are wedge surfaces, the octahedron forms an octahedral wedge body small on the top and large on the bottom. The wedge body 410 on the lower end may be of a roughly symmetrical structure to that of the wedge body 410 on the upper end and will not be described again.

With reference to the locking part 30 in FIG. 5, the slot 32, in combination with two wedge ends 410 of the locking tongue 41, roughly forms an octahedral shape provided with the opening (33) and has inner walls 321, 322, 323, and 324.

Figure 8:
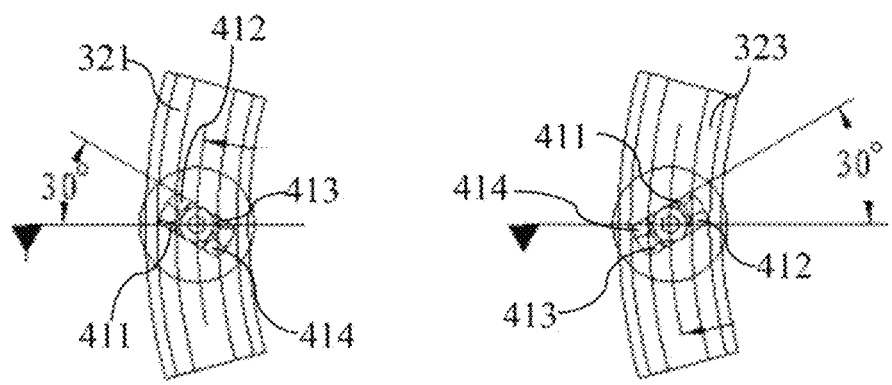
FIG. 8 schematically illustrates a state diagram of a locking tongue of the engaging part engaged with a slot of the locking part.

FIG. 8 schematically illustrates a state diagram of the locking tongue 41 engaged with the slot 32. The left side of FIG. 8 illustrates the state of the locking tongue 41 rotating clockwise to be engaged with the slot 32, and the right side of FIG. 8 illustrates the state of the locking tongue 41 rotating anticlockwise to be engaged with the slot 32. With reference to FIG. 5 to FIG. 8, the inner wall 321 of the slot 32 may be used for making contact with the wedge surface 411 or 412 (the inner wall 321 may be in contact with the wedge surface 411 when the locking tongue 41 rotates clockwise, and the inner wall 321 may be in contact with the wedge surface 414 when the locking tongue 41 rotates anticlockwise). Similarly, the inner wall 322 of the slot 32 may be used for making contact with the wedge surface 415 or 418, the inner wall 323 of the slot 32 may be used for making contact with the wedge surface 412 or 413, and the inner wall 324 of the slot 32 may be used for making contact with the wedge surface 416 or 417.

By means of the aforementioned engagement, the degree of engagement between the locking tongue 41 and the inner walls of the slot 32 is less affected by the wear between the locking tongue 41 and the inner walls of the slot 32. For example, when the engaging wedge surfaces of the locking tongue and the inner walls of the slot wear, the engaging part 40 is driven by the driving part 50 to rotate by a larger angle to tighten the engaging part and the locking part.

The aforementioned wedge ends 410 and wedge surfaces may further have at least one of the following other features so that the locking tongue 41 can abut against the inner walls of the slot 32 more closely: the length of each wedge end 410 in the vertical direction thereof gradually decreases in the longitudinal direction thereof, for example, cross-sections of the aforementioned two wedge ends 410 in the X-Y (X and Y are respectively the vertical direction and longitudinal direction of the locking tongue 40) plane are roughly trapezoids; each wedge surface is disposed at the edge of the wedge end, for example, the wedge surfaces 411 to 418 are respectively disposed at corners of the locking tongue 41; the thickness of each wedge end in the traverse direction thereof gradually increases from one side to another side of a wedge surface thereof, for example, a cross-section of each wedge end at a pair of wedge surfaces 411 and 415 thereof in the Y-Z (Z is the traverse direction of the locking tongue 41) plane is a trapezoid.

The engaging part 40 further includes a rotating shaft 42, where the locking tongue 41 is formed on one end of the rotating shaft 42. The driving part 50 may include a motor, where the motor may be connected to the other end of the rotating shaft 42 to rotate the engaging part 40 to the initial position or the locked position. Specifically, the motor controls the rotating shaft 42 to drive the locking tongue 41 to rotate, so as to be snapped into or released from the slot 32 of the locking part 30.

The scan gantry in this embodiment may further include a locking controller used for supplying power to the motor so that the motor rotates or keeps the torque, or the locking controller may further be used for supplying power that is for adding hydraulic pressure to a locking piece driving mechanism, where the locking piece driving mechanism will be described later. The aforementioned locking controller may be connected to the controller 166 shown in FIG. 1 or may be a part of the controller 166. In an application scenario, when the tilt supporting frame 20 is in a non-tilted state, the control mechanism of the medical imaging system may control, in response to a tilting control signal (for example, sent by the controller 164), the tilt supporting frame 20 to rotate to tilt at a specific angle; after the tilting is completed, the motor may rotate the engaging piece 40 in response to a locking control signal (for example, sent by the locking controller or the controller 166) and drive the locking tongue 41 to rotate to be engaged with the slot 32 so as to lock the bottom supporting frame 10 and the tilt supporting frame 20; after secure locking, the control mechanism of the medical imaging system may control, in response to a rotation control signal (for example, sent by the controller 161), the rotating part of the scan gantry to rotate at a high speed; after the rotating part stops rotating, the motor reversely rotates the engaging part 40 in response to an unlocking control signal (for example, sent by the locking controller or the controller 166), and drives the locking tongue 41 to rotate back to the initial position, so as to unlock the bottom supporting frame 10 and the tilt supporting frame 20; after the unlocking, the control mechanism of the medical imaging system may control the tilt supporting frame 20 to tilt in response to a scan gantry reset signal (for example, sent by the controller 164).

Further, the locking mechanism 16 of the scan gantry in this embodiment further includes a fixing part 60 disposed on the bottom supporting frame 10, where the fixing part 60 clamps the rotating shaft 42 to prevent the engaging part from rotation and axial movement when the tilt supporting frame 20 is in the locked state. As shown in FIGS. 7 and 8, the rotating shaft 42 includes a shaft rod 421 and a shaft disk 422 radially extending outward from the shaft rod 421. The rotating shaft 42 and/or shaft disk 422 may be used, in combination with the fixing part 60, for preventing the engaging part 40 from rotation and axial movement when the tilt supporting frame 20 is in the locked state. In an embodiment, at the locked position, the motor of the driving part 50 keeps the motor torque until the engaging part 40 is clamped by the fixing part 60.

The structure and working mode of the fixing part are described in detail below with reference to the accompanying drawings.

The locking mechanism 16 shown in FIG. 4 further includes the fixing part 60. To facilitate observation of the internal structure of the clamping part 60, FIG. 9 illustrates a sectional view of the locking mechanism 16 in FIG. 4, FIG. 10 illustrates a supporting body 61 in FIG. 4, FIG. 11 illustrates a matching structure of a locking piece 63 with an upper supporting body 613 removed and the engaging part 40 in FIG. 10, and FIG. 12 illustrates a lower supporting body 611 in FIG. 11.

Figure 9:
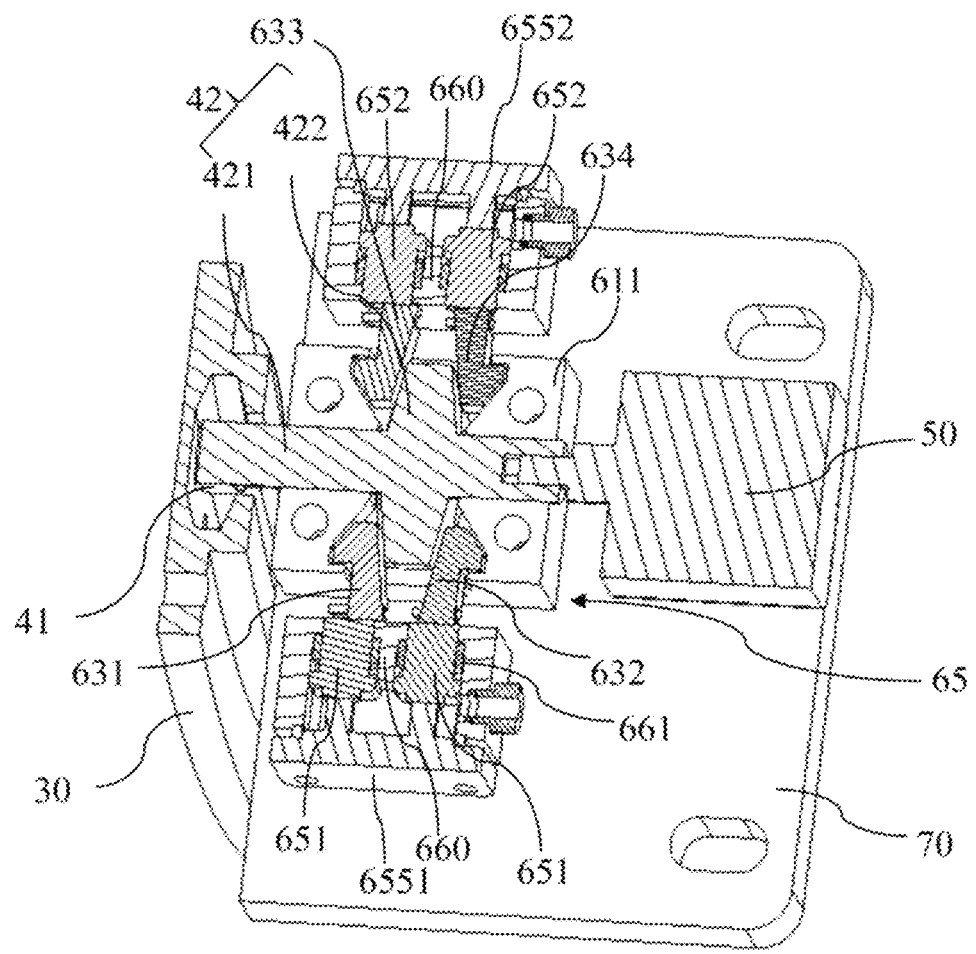
FIG. 9 illustrates a sectional view of the locking mechanism in FIG. 4.
Figure 10:
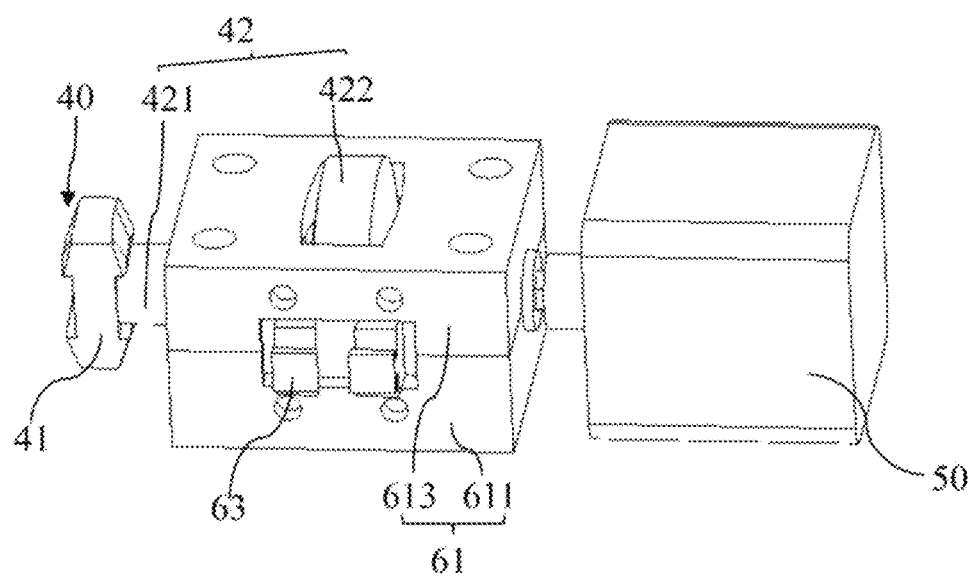
FIG. 10 illustrates a supporting body in FIG. 4.

With reference to FIG. 4, FIG. 9, and FIG. 10, the fixing part 60 includes a supporting body 61, a locking piece 63, and a locking piece driving mechanism 65. The fixing part 60 may be mounted on a fixing plate 70. The supporting body 61 may include a lower supporting body 611 and an upper supporting body 613.

Figure 11:
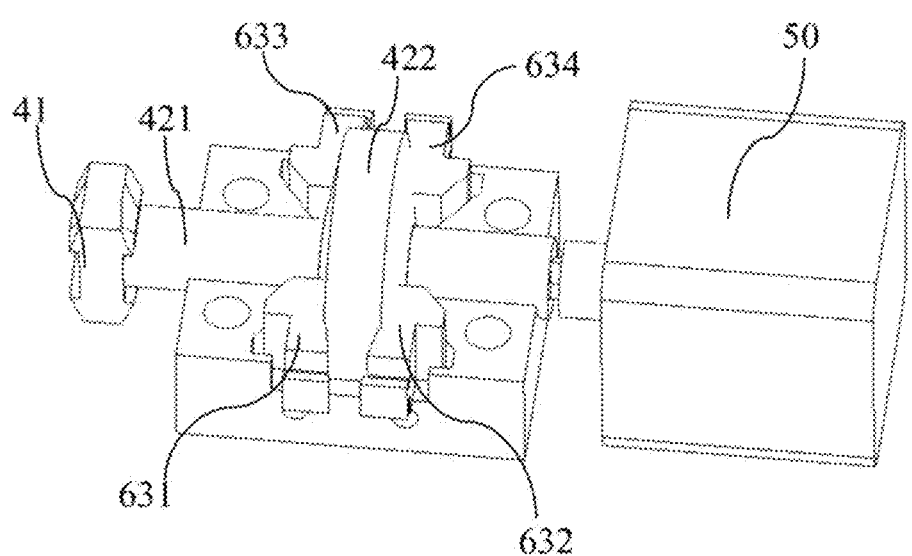
FIG. 11 illustrates a matching structure of a locking piece with an upper supporting body removed and the engaging part in FIG. 10.
Figure 12:
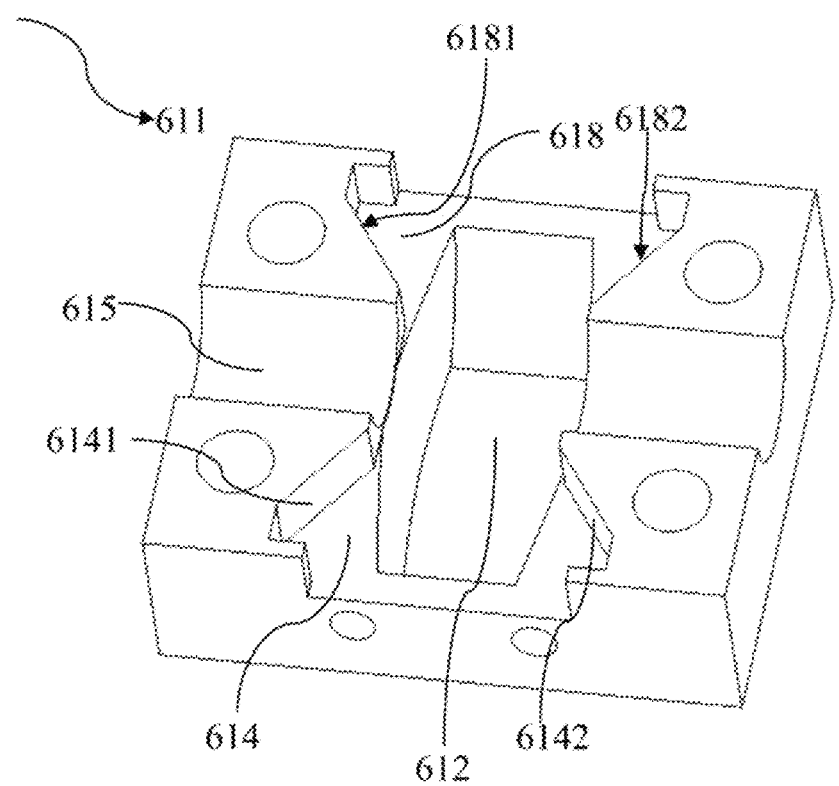
FIG. 12 illustrates a lower supporting body in FIG. 11.

With reference to FIG. 9, FIG. 11, and FIG. 12, the supporting body 61 is provided with a recess 615 for accommodating the rotating shaft 42 as well as a guide groove in communication with the recess 615. The locking piece 63 is at least partially disposed in the guide groove and in contact with the rotating shaft 42. The structure of the lower supporting body 611 has been shown in FIG. 12. Those skilled in the art should understand that the upper supporting body 613 may have a roughly symmetrical structure to that of the lower supporting body 611 to together accommodate the engaging part 40 and at least part of the locking piece 63, which will not be described herein again.

With further reference to FIG. 12, the supporting body 61 is further provided with an opening 612 for accommodating the shaft disk 422 of the rotating shaft 42. The aforementioned guide groove is in communication with the opening 612 so that the locking piece 63 accommodated therein can clamp the shaft disk 422.

In an embodiment, the aforementioned guide groove may include a first guide groove 614 and a second guide groove 618 respectively disposed on two sides of the rotating shaft 42. The first guide groove 614 includes two side walls 6141 and 6142 distributed on two sides of the opening 612. The second guide groove includes two side walls 6181 and 6182 distributed on two sides of the opening 612.

In an embodiment, as shown in FIG. 9 and FIG. 11, the locking piece 63 may include two first wedge blocks 631 and 632 as well as two second wedge blocks 633 and 634. The two first wedge blocks 631 and 632 are partially disposed in the first guide groove 614 and oppositely located on two sides of the shaft disk 422. The two second wedge blocks 633 and 634 are partially disposed in the second guide groove 618 and oppositely located on two sides of the shaft disk 422.

In an embodiment, as shown in FIG. 9 and FIG. 11, the two side walls 6141 and 6142 of the first guide groove 614 each form a wedge space with the shaft disk 422 to respectively match the first wedge blocks 631 and 632; the two side walls 6181 and 6182 of the second guide groove 618 each form a wedge space with the shaft disk 422 to respectively match the second wedge blocks 633 and 634. The two first wedge blocks 631 and 632 and the two second wedge blocks 633 and 634 can move within a certain range toward the shaft rod 421 in their respective wedge space. While moving toward the shaft rod 421, the first wedge blocks and the second wedge blocks gradually increase the pressure (or friction) applied on the shaft disk 422 and the two side walls 6141 and 6142 of the first guide groove 614 or the two side walls 6181 and 6182 of the second guide groove 618 until the shaft disk 422 is clamped so that the engaging part 40 cannot further rotate or axially move. While moving away from the shaft rod 421, the first wedge blocks and the second wedge blocks gradually decrease the pressure (or friction) applied on the shaft disk 422 and the side walls 6141, 6142, 6181, and 6182 until the engaging part 40 is released so that the engaging part 40 can rotate and axially move.

With reference to FIG. 4 and FIG. 9, the locking piece driving mechanism 65 is used for applying a driving force to the locking piece 63 so that the locking piece 63 clamps the engaging part 40. In a usage scenario, the locking piece driving mechanism 65 may drive the locking piece 63 to clamp the engaging part 40 to prevent it from rotation and movement in response to the aforementioned rotation control signal (or other signals capable of indicating that the tilt supporting frame 20 is to be locked); the locking piece driving mechanism 65 may further retract the locking piece 63 upon an unlocking control signal to release the engaging part 40, so that the driver 50 can drive the engaging part 40 to rotate between the initial position and the locked position.

Figure 13:
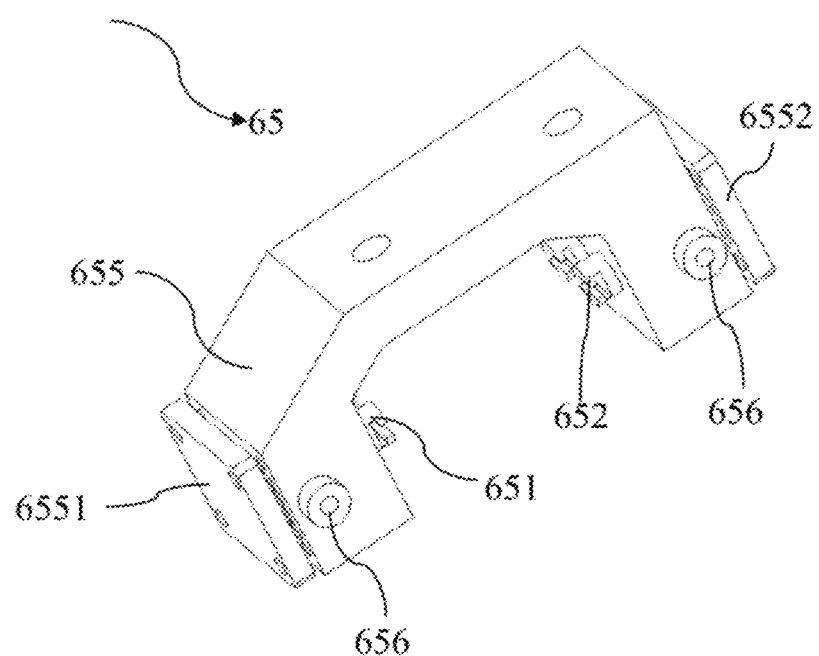
FIG. 13 and FIG. 15 both illustrate a locking piece driving mechanism in FIG. 4.
Figure 14:
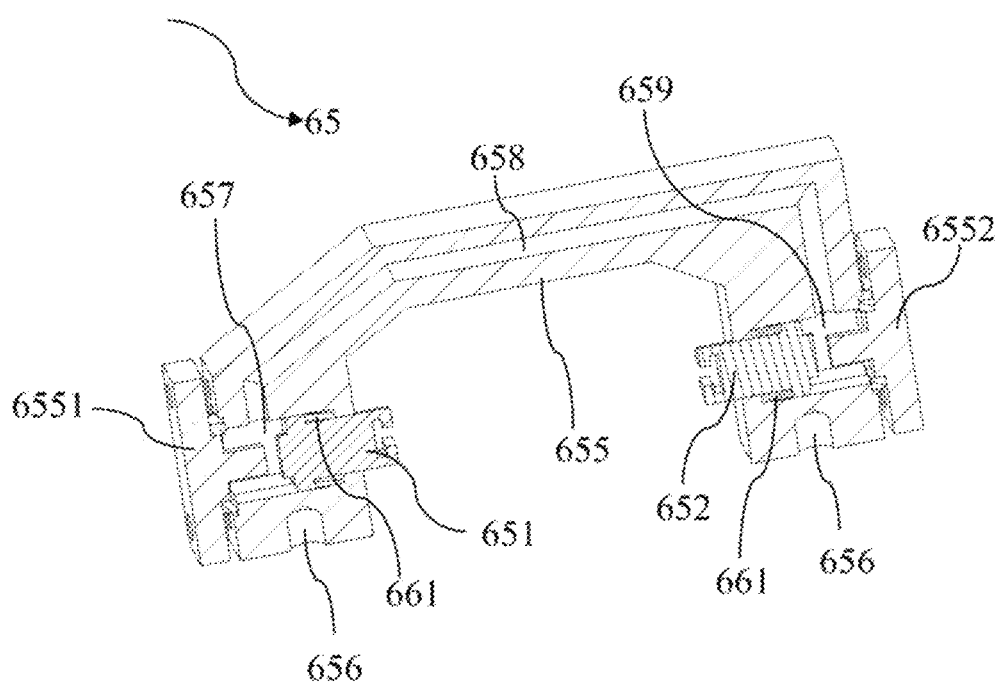
FIG. 14 illustrates a sectional view of the locking piece driving mechanism in FIG. 13.
Figure 15:
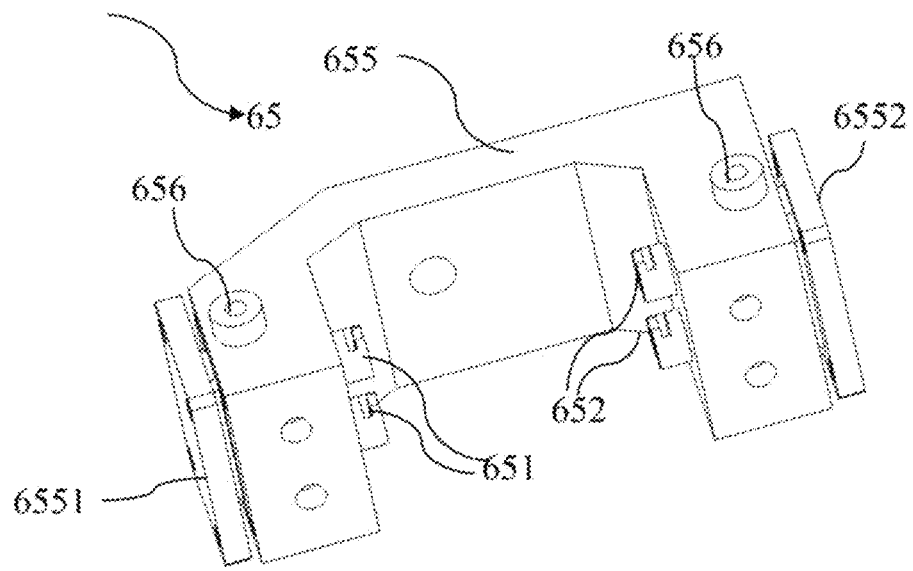
Figure 16:
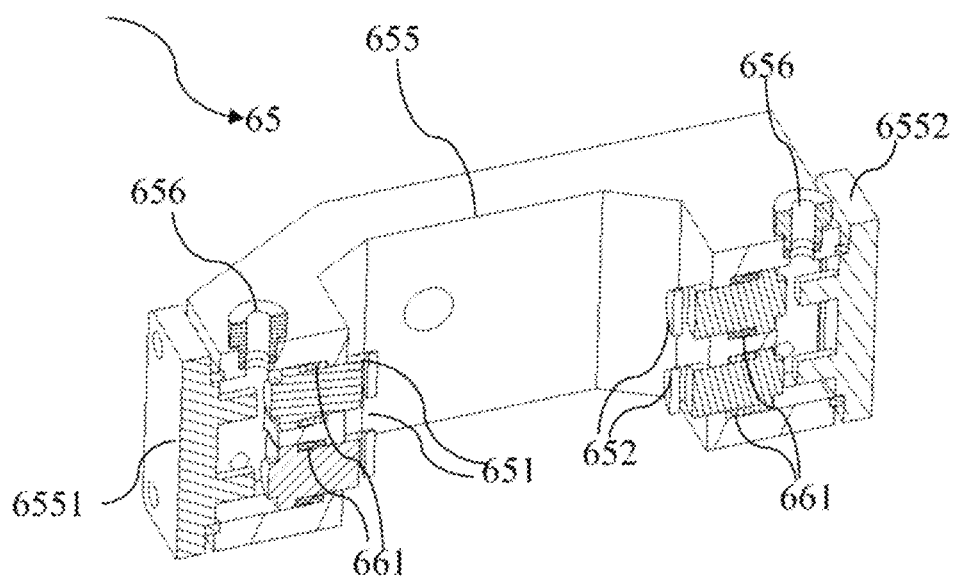
FIG. 16 illustrates a sectional view of the locking piece driving mechanism in FIG. 15.

FIG. 13 and FIG. 15 both illustrate the locking piece driving mechanism 65 in FIG. 4. FIG. 14 illustrates a sectional view of the locking piece driving mechanism 65 in FIG. 13, and FIG. 16 illustrates a sectional view of the locking piece driving mechanism 65 in FIG. 15. With reference to FIG. 4, FIG. 9, and FIGS. 13 to 16, the locking piece driving mechanism 65 includes a hydraulic component, where the hydraulic component includes a housing 655, a valve rod, and a nozzle 656. A hydraulic cavity is formed in the housing 655. One end of the valve rod is disposed in the hydraulic cavity, and the other end extends out of the housing 655 to be connected to the locking piece 63. The nozzle 656 is in communication with the hydraulic cavity and used for injecting liquid into the hydraulic cavity to push the valve rod to move the locking piece 63 so as to apply pressure to the locking piece 63, or discharging liquid from the hydraulic cavity and pulling back the valve rod under a resilience force of an elastic sealing piece 661 to retract the locking piece 63 so as to release the pressure of the locking piece 63 on the engaging part 40.

In an embodiment, the scan gantry of mobile medical equipment is already provided with a hydraulic device, and the nozzle 656 may be in communication with the existing hydraulic device so as to inject liquid into the hydraulic cavity.

In this embodiment, the hydraulic cavity may include a first cavity 657 and a second cavity 659. The first cavity 657 and the second cavity 659 are respectively disposed on two ends of the housing 655. The housing 655 is further provided with a hydraulic pipe 658 in communication with the first cavity 657 and the second cavity 659. In an embodiment, the first cavity 657 and the second cavity 659 each have two independent chambers, and the four chambers communicate so that four valve rods are under equal hydraulic pressure, such that the locking piece 63 exerts equal clamping force on the engaging part 40.

The aforementioned valve rods include two first valve rods 651 and two second valve rods 652. One end of each first valve rod 651 is disposed in the first cavity 657 (for example, in an independent chamber of the first cavity), and one end of each second valve rod 652 is disposed in the second cavity 659 (for example, in an independent chamber of the second cavity). The other ends of the two first valve rods 651 respectively extend out of the housing 655 to be correspondingly connected to the two first wedge blocks 631 and 632, and the other ends of the two second valve rods 652 respectively extend out of the housing 655 to be correspondingly connected to the two second wedge blocks 633 and 634.

Further, the two first valve rods 651 as well as the two second valve rods 652 are separately placed on the housing 655, for example, separated by a spacer 660 to avoid mutual interference.

Further, an elastic sealing piece 661 is disposed between each first valve rod 651 and the housing 655 as well as between each second valve rod 652 and the housing. The elastic sealing piece achieves sealing and guides/limits the moving direction of the corresponding valve rods.

Further, the housing 655 is provided with two openings respectively causing the first cavity 657 to be in communication with the outside and the second cavity 659 to be in communication with the outside, and the housing 655 further has two covers 6551 and 6552 connected thereto. The two covers 6551 and 6552 are respectively used for blocking the aforementioned two openings of the housing 655. In this way, members in the housing 655 can be conveniently assembled, dissembled, and repaired.

Figure 17:
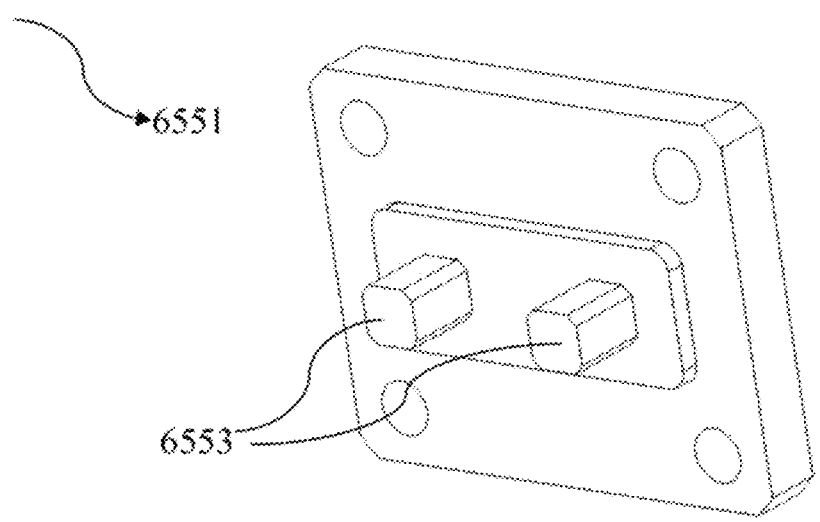
FIG. 17 illustrates a cover in FIG. 13.

With reference to FIG. 17, FIG. 17 illustrates the covers 6551 & 6552 in FIG. 13. Each cover 6551/6552 of the housing 655 is provided with stop protrusions 6553 for stopping two corresponding first valve rods or two corresponding second valve rods, so as to avoid excessively large range of return movement of the first valve rods 651 or the second valve rods 652 after pressure is released.

The structures of the aforementioned wedge blocks and valve rods and the connection mode thereof are described below with reference to the accompanying drawings.

Figure 18:
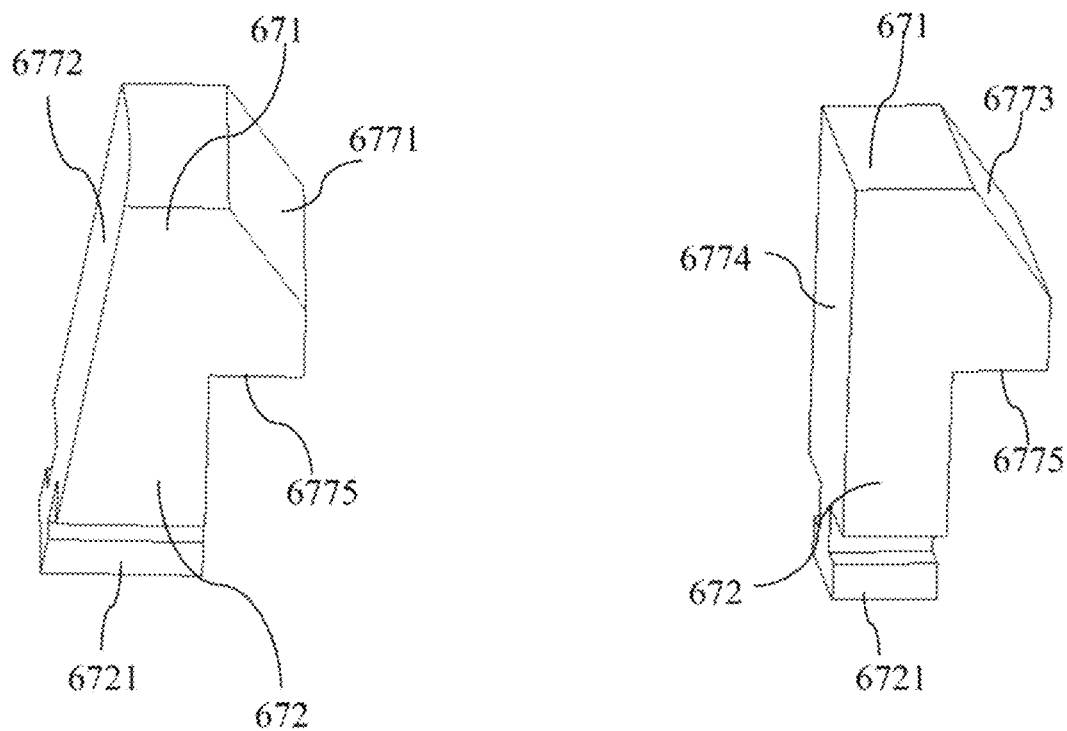
FIG. 18 illustrates wedge blocks of the locking piece in FIG. 11.

With reference to FIG. 18, FIG. 18 further illustrates wedge blocks of the locking piece 63 in FIG. 11. Each wedge block includes a first wedge block end 671 and a second end 672. The first wedge block end 671 may be disposed in the aforementioned corresponding wedge space to match the rotating disk 422, and the second end 672 is used for connecting to a corresponding valve rod. As shown in the figure to the left in FIG. 18, in an embodiment, the first wedge block end 671 includes a curved surface 6771 and a tilted surface 6772. The tilted surface 6771 is used for matching one side wall of a corresponding guide groove. The curved surface 6772 is used for matching the rotating disk 422. In other words, the curve of the side surface of the rotating disk 422 is consistent with the curve of the curved surface 6772. As shown in the figure to the right in FIG. 18, in another embodiment, the first wedge block end 671 includes two opposite surfaces 6773 and 6774. The surface 6773 is a tilted surface used for matching one side wall of the corresponding guide groove. The surface 6774 is used for matching the rotating disk 422, and the surface 6774 matching the rotating disk 422 may be not tilted. In other words, the side surface of the rotating disk 422 and the surface 6774 are surfaces perpendicular to the axis direction of the engaging part 40.

Further, the first wedge block end 671 of each wedge block further includes a stop bottom surface 6775 that is opposite to one wall of the guide groove in the moving direction of the wedge block so as to perform stopping during return movement.

Figure 19:
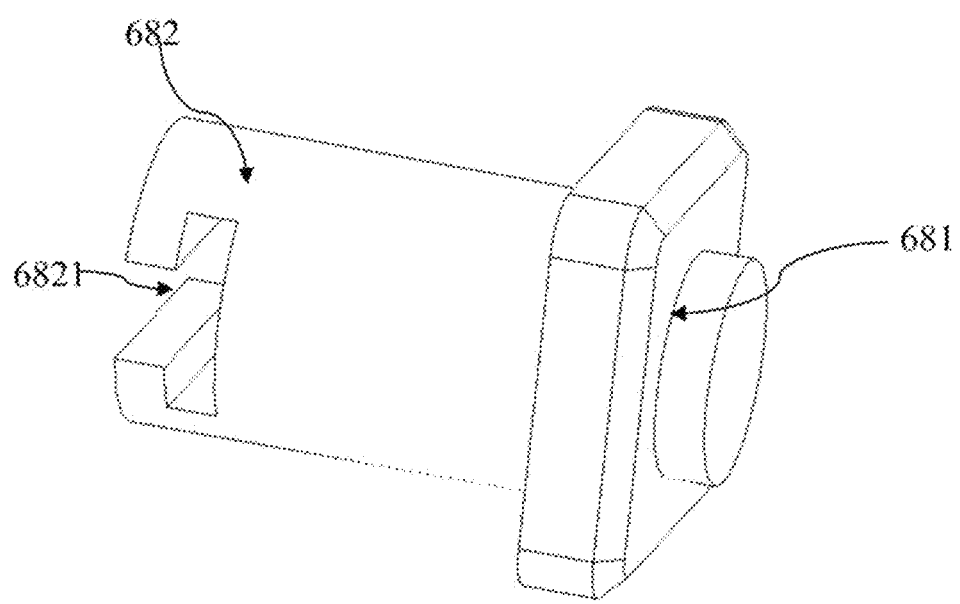
FIG. 19 illustrates a valve rod in FIG. 13.

With reference to FIG. 19, FIG. 19 further illustrates the valve rods 651 & 652 in FIG. 13. Each valve rod includes a first end 681 and a second end 682. The first end 681 is disposed in a corresponding cavity 657 & 659 of the housing 655 of the hydraulic cavity so that it can be driven to reciprocate. The first end 681 is provided with a square stopper to avoid free rotation of the valve rod by means of the characteristic that a square does not rotate easily.

Figure 20:
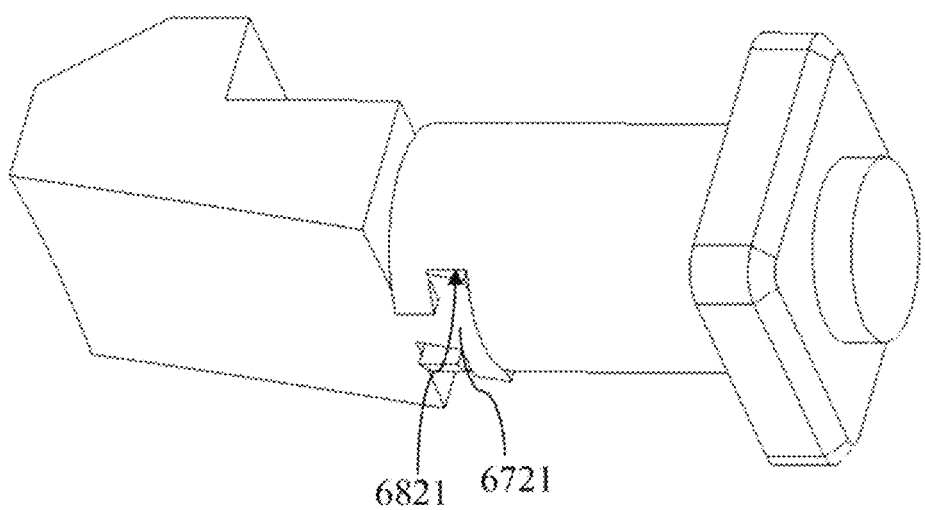
FIG. 20 illustrates a connection mode of the wedge block and the valve rod in an embodiment.

With continuing reference to FIG. 20, FIG. 20 illustrates a connection mode in an embodiment of the wedge blocks 631, 632, 633, and 634 and the valve rods 651 & 652. In this embodiment, the valve rod is movably connected to the locking piece 63 so that the locking piece 63 has a certain movement margin with respect to the valve rod. In this way, reduced clamping efficiency caused by mechanical errors in the process that the locking piece 63 clamps the engaging part 40 is avoided.

For example, in an implementation manner, the second end 672 of the wedge block shown in FIG. 18 is formed with a T-shaped protrusion 6721, the second end 682 of the valve rod shown in FIG. 19 is formed with a T-shaped groove 6821, the T-shaped protrusion 6721 and the T-shaped groove 6821 are disposed matching each other, and walls of the T-shaped protrusion 6721 and the T-shaped groove 6821 may have a certain gap so that the T-shaped protrusion 6721 can have some moving space at different angles while achieving stable connection, and the T-shaped protrusion 6721 can slide relatively in the length direction of the T-shaped groove to adapt to the positional change of the locking piece along the T-shaped groove of the valve rod during clamping and releasing of the locking piece.

By means of the aforementioned structure of the wedge block and the connection mode thereof to the valve rod, even if mechanical errors or influence in other aspects may exist, the effective clamping of the engaging part 40 can be ensured by flexibly controlling the wedge blocks in the process of clamping the engaging part 40 by the locking piece 63. This advantage will be described through the examples shown in FIG. 9 and FIGS. 21 and 22.

Figure 21:
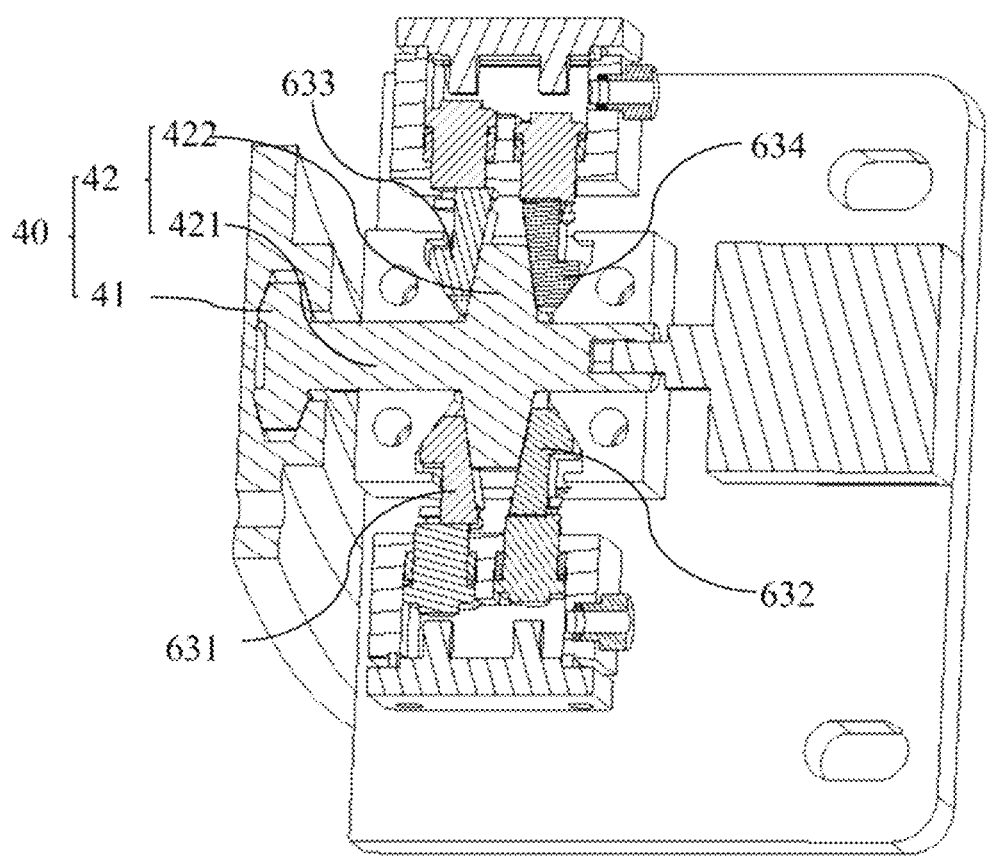
FIG. 21 and FIG. 22 each illustrate a state of the locking piece clamping the engaging part when different mechanical errors exist.
Figure 22:
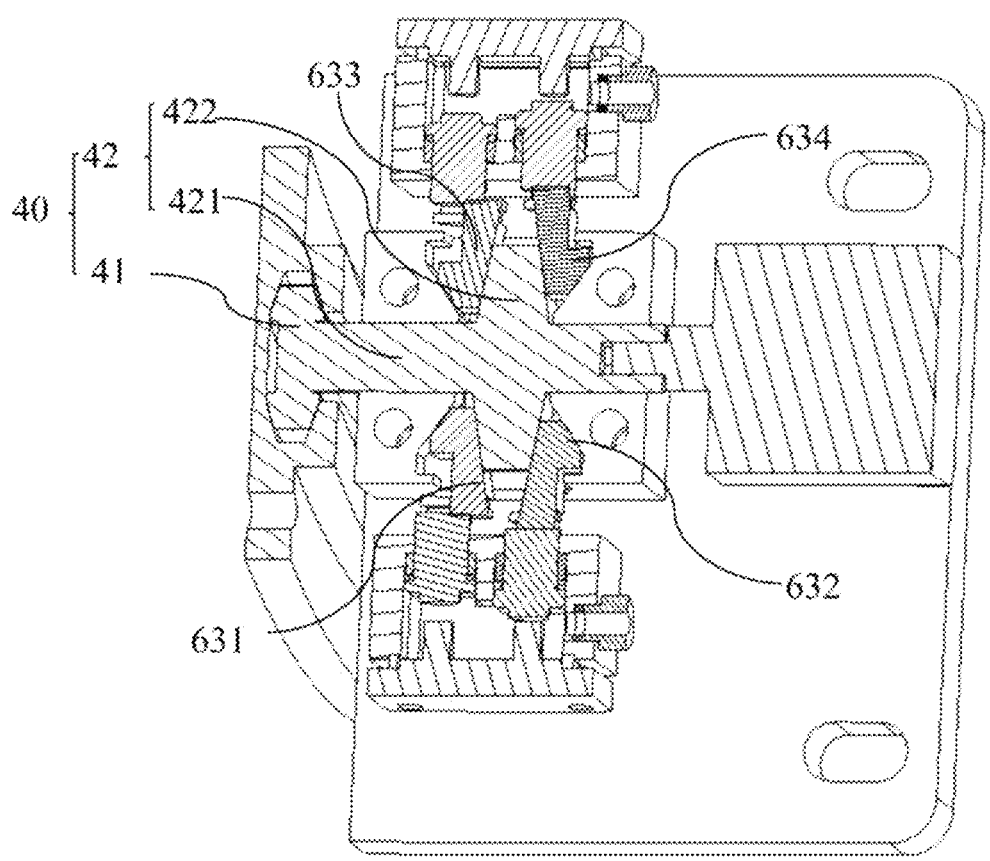

By means of the wear of the side wall of the guide groove and the tilted surface of the locking piece, the locking piece can be pushed out by the valve rod of the locking piece driving mechanism for a longer stroke to clamp the shaft disk. FIG. 9 illustrates a state of the locking piece 63 clamping the engaging part 40 in an ideal state. Under the same locking piece driving force, it can be seen that the four wedge blocks are distributed symmetrically. FIGS. 21 and 22 each illustrate a state of the locking piece 63 clamping the engaging part 40 when different mechanical errors exist. It can be seen that the two wedge blocks on the right side of FIG. 21 are closer to the shaft rod 421 than the two wedge blocks on the left side, because when the tilt supporting frame 20 is at different tilting angles, the slot 32 of the locking part 30 moves inward due to errors, resulting in larger wedge space on the right side. However, since the clamping mode of the wedge structure and the movable connection mode of the wedge block and the valve rod, the clamping efficiency is less affected by such errors. Similarly, the two wedge blocks on the left side of FIG. 22 are obviously closer to the shaft rod 421 than the two wedge blocks on the right side.

The scan gantry in this embodiment may further include a sensor for sensing the locked state of the tilt supporting frame 20. The control mechanism may generate a corresponding control signal based on a sensing signal of the sensor. For example, a rotation control signal may be generated when it is sensed that the tilt supporting frame 20 is already locked, and a tilting control signal may be generated when it is sensed that the tilt supporting frame 20 is already unlocked. A plurality of sensors described above may exist, and may be disposed on, for example, the inner walls of the slot 32, the shaft disk 422 of the engaging part 40, or the side walls of the guide groove, so as to generate a sensing signal when sensing pressure.

Scan Gantry in Second Embodiment

The scan gantry in this embodiment is similar to the scan gantry in the first embodiment in terms of structure, connection mode, and working mode. For example, like the bottom supporting frame 10 and the tilt supporting frame 20 in FIG. 2 and FIG. 3, the scan gantry in this embodiment may further include a bottom supporting frame 10 and a tilt supporting frame 20 that are connected to each other, where the tilt supporting frame 20 can be tilted relative to the bottom supporting frame 10. The scan gantry in this embodiment of the present invention also includes a locking mechanism.

Figure 23:
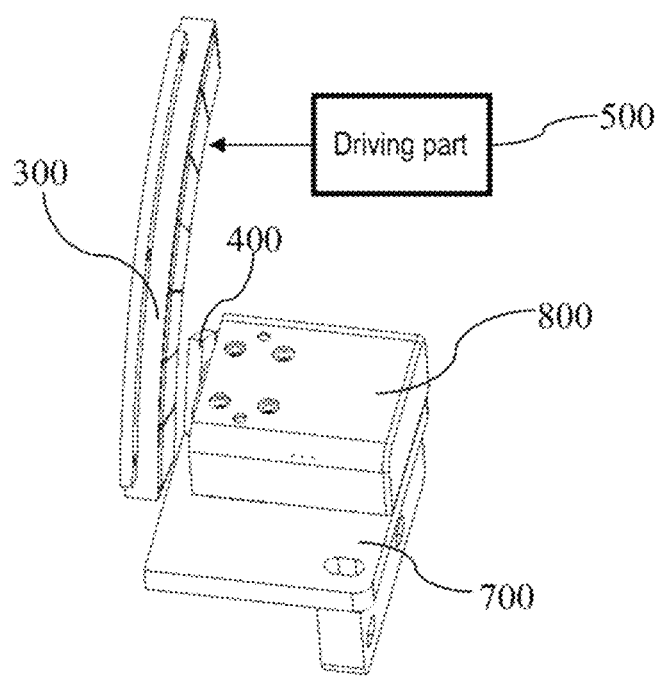
FIG. 23 illustrates a locking mechanism of a scan gantry in a second embodiment.

With reference to FIG. 23, FIG. 23 illustrates the locking mechanism in this embodiment. The locking mechanism includes a primary electromagnetic component 300 of a locking part 30, an engaging part 400, and a driving part 500, and may further include a fixing part 600 and a shielding case 800.

With reference to FIGS. 2 and 3 and FIG. 23, the primary electromagnetic component 300 is disposed on the tilt supporting frame 20 according to a tilt trajectory of the tilt supporting frame 20. Specifically, the effective size of the primary electromagnetic component 300 is related to the maximum tilting range of the tilt supporting frame 20. For example, when the tilt supporting frame 20 is tilted at the maximum angle, the primary electromagnetic component 300 has a large enough size to lock the tilt supporting frame 20. More specifically, the shape of the effective portion of the primary electromagnetic component 300 is related to the moving trajectory of the tilt supporting frame 20. For example, the effective portion of the primary electromagnetic component 300 forms an arc shape with a radian matching the radian of the tilt trajectory of the tilt supporting frame 20, so that the locking mechanism can lock the tilt supporting frame 20 when the tilt supporting frame 20 is at any position within the tilting range thereof. For example, the tilt trajectory of the tilt supporting frame 20 is a segment of circular arc. The primary electromagnetic component 300 is disposed on the tilt supporting frame 20 according to the tilt trajectory and extends to form another segment of circular arc concentric with the aforementioned segment of circular arc.

The engaging part 400 is disposed on the bottom supporting frame 10 and used for, at any tilted position, engaging with the primary electromagnetic component 300 and locking the tilt supporting frame 20 relative to the bottom supporting frame 10, or used for unlocking the primary electromagnetic component 300 from the tilt supporting frame 20.

The driver 500 is used for driving the engaging part 400 to move to a locked position or driving the engaging part 400 to return to an initial unlocked position.

In this embodiment, the engaging part 40 may be mounted on the bottom supporting frame by means of a fixing plate 700. For example, the fixing plate 700 is fixed to the bottom supporting frame by means of screws or other mounting methods and carries thereon the engaging part 400.

The structure, connection mode, and working principles of the primary electromagnetic component 300 of the locking part 30, the engaging part 400, and the driving part 500 are further described below with reference to the accompanying drawings.

Figure 24:
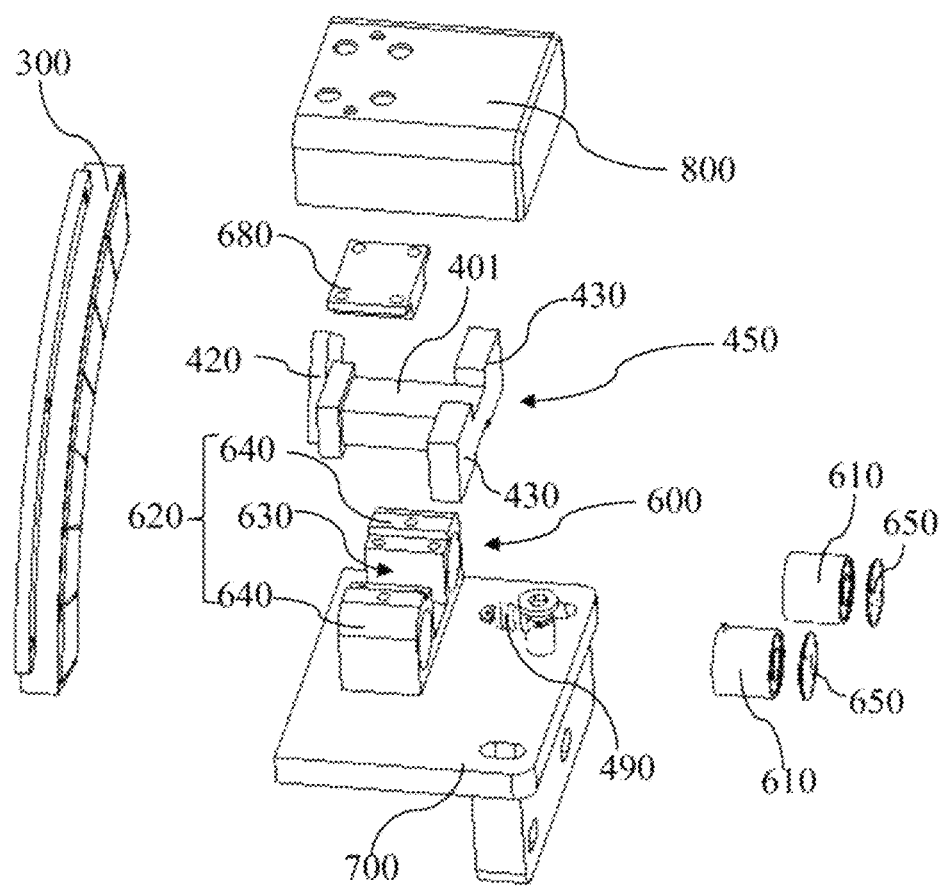
FIG. 24 illustrates an exploded structure of the locking mechanism in FIG. 23.
Figure 25:
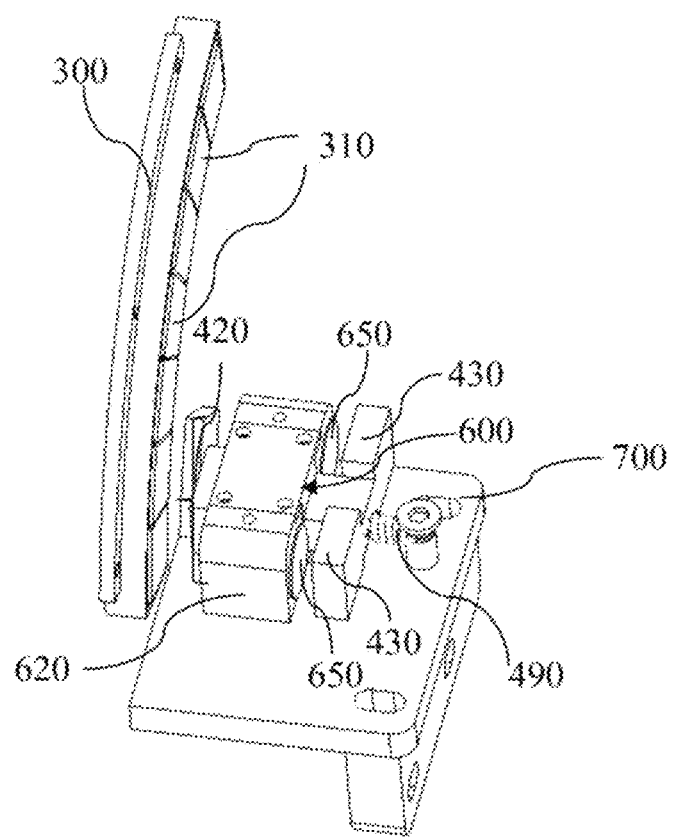
FIG. 25 illustrates a portion in FIG. 23 with a shielding case removed.

FIG. 24 illustrates an exploded structure of the locking mechanism in FIG. 23, and FIG. 25 illustrates a portion of the engaging part 40 blocked by the shielding case in FIG. 23. With reference to FIGS. 23 to 25, the locking part 300 includes electromagnetic units 310 extending into an arc shape. In other embodiments, the primary electromagnetic component 300 may also be configured as a surface, the size of which is determined so as to cover the required arc trajectory.

The engaging part 400 is a movable magnetic core 450. One end of the movable magnetic core 450 is connected to the fixing plate 700 by means of an elastic component 490. For example, the elastic component may be an extension spring with one end fixed to the fixing plate 700 and the other end connected to the movable magnetic core 450.

The driving part 500 is used for controlling the movable magnetic core 450 to move toward the primary electromagnetic component 300 so that the movable magnetic core 450 is attracted to the primary electromagnetic component 300. At this time, the elastic component 490 is stretched. Specifically, the driving part 500 includes a power controller (not shown) electrically connected to the primary electromagnetic component 300. In a usage application, the power controller is used for providing a current to the primary electromagnetic component so that the primary electromagnetic component 300 attracts the movable magnetic core 450. For example, the power controller may, in response to a locking control signal, cause the primary electromagnetic component 300 to generate an attraction force on the movable magnetic core 450 opposite thereto. Driven by the attraction force, the movable magnetic core 450 moves toward the primary electromagnetic component 300 to the locked position by overcoming the pulling force of the elastic component 490 and is attracted to the primary electromagnetic component 300. When the power controller stops supplying power to the primary electromagnetic component, the primary electromagnetic component 300 releases the movable magnetic core 450. For example, the power controller may, in response to an unlocking control signal, cause the primary electromagnetic component 300 to lose the attraction force on the movable magnetic core 450, and the movable magnetic core 450 returns to the initial position under the force of the elastic component 490.

In an embodiment, the aforementioned fixing part 600 is disposed on the bottom supporting frame 10. For example, the fixing part 600 may be disposed on the bottom supporting frame 10 by means of the fixing plate 700. The movable magnetic core 450 may be supported and guided by the fixing part 600. For example, the fixing part 600 allows only axial movement of the movable magnetic core 450 and disallows movement of the movable magnetic core 450 in other directions. The fixing part 600 may further fix the movable magnetic core 450 to prevent further movement of the movable magnetic core 450 when the movable magnetic core 450 is attracted to the primary electromagnetic component 300. In this way, the movable magnetic core 450 can be stabilized in the locked state.

In an embodiment, the fixing part 600 includes a secondary electromagnetic component 610. The movable magnetic core 450 includes a primary attracting part 420 located on the side of the primary electromagnetic component 300 and a secondary attracting part 430 located on the side of the secondary electromagnetic component. The primary attracting part 420 is opposite to the primary electromagnetic component 300 so as to be attracted to the primary electromagnetic component 300, and the secondary attracting part 430 is opposite to the secondary electromagnetic component 610 so as to be attracted to the secondary electromagnetic component 610.

The fixing part 600 further includes an elastic soft magnetic pad 650 fixed to the secondary electromagnetic component 610. The elastic soft magnetic pad 650 is elastic when not magnetic, and is used for compensating the gap between the secondary electromagnetic component 610 and the movable magnetic core 450 after the movable magnetic core 450 is attracted to the primary electromagnetic component 300, thereby ensuring reliable attraction between the secondary electromagnetic component and the movable magnetic core. The elastic soft magnetic pad 650 hardens when magnetic.

For example, two elastic soft magnetic pads 650 are respectively fixed to two secondary electromagnetic components 610 and used for adapting to the change of the gap between the secondary electromagnetic components 610 and the secondary attracting parts 430 of the movable magnetic core 450 by means of the elastic compressibility of the elastic soft magnetic pads 650 after the movable magnetic core 450 is first attracted by the primary electromagnetic component 300, and meanwhile ensuring close contact and attraction between the secondary electromagnetic components 610 and the secondary attracting parts 430 of the movable magnetic core 450 by means of the magnetism of the elastic soft magnetic pads 650.

In an embodiment, the movable magnetic core 450 roughly forms a T-shaped structure, including a connection body 401 forming the backbone of the T-shaped structure. The primary attracting part 420 is disposed on one end of the connection body 401, and the secondary attracting parts 430 are disposed on the other end of the connection body 401, where two secondary attracting parts 430 exist and are oppositely disposed on two sides of the connection body 401 respectively.

The fixing part 600 further includes a lower supporting body 620 and an upper supporting body 680. The lower supporting body 620 is provided with a recess 630 and two secondary electromagnetic mounting end portions 640 on two sides of the recess 630. The two secondary electromagnetic components 610 are respectively mounted in an embedded manner in one ends of the two secondary electromagnetic mounting end portions 640 close to the elastic component 490. The connection body 401 of the movable magnetic core 450 is disposed in the recess 630, the primary attracting end portion 420 thereon is opposite to the primary electromagnetic component 300, and the two secondary attracting parts 430 are respectively opposite to the two secondary electromagnetic components 610.

Although two secondary attracting parts are shown in the figure, those skilled in the art should understand that more or larger secondary attracting parts and corresponding secondary electromagnetic components may be provided so as to achieve more stable attraction.

The power controller of the driving part 500 may further be electrically connected to the secondary electromagnetic components 610 so as to attract a corresponding secondary attracting part 430 to fix the movable electromagnetic core in response to a locking control signal, or release the movable electromagnetic core 450 in response to an unlocking control signal.

Figure 26:
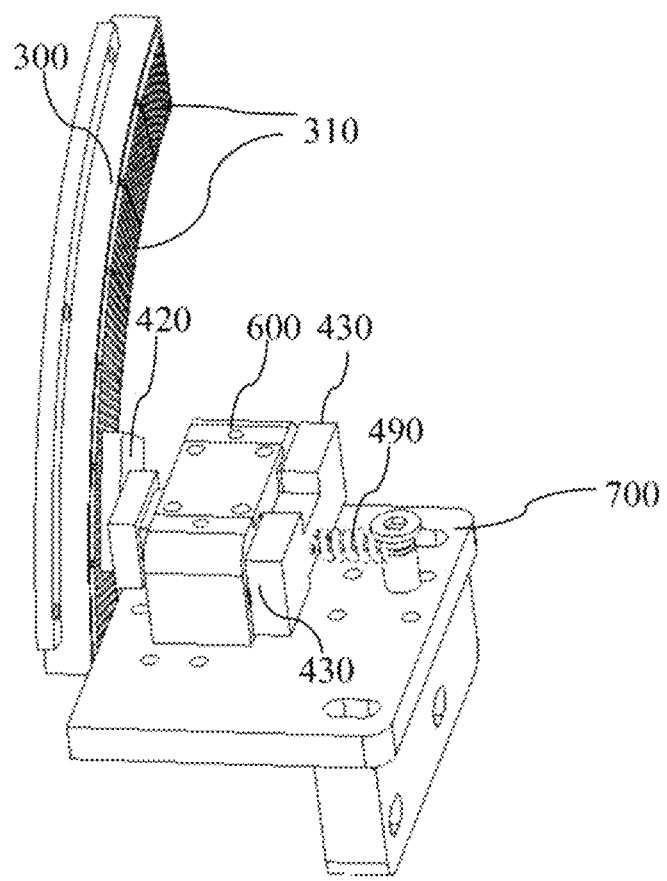
FIG. 26 illustrates a state when a movable magnetic core is attracted to a primary electromagnetic component and a secondary electromagnetic component.

With reference to FIG. 26, FIG. 26 illustrates a state when the movable magnetic core 450 is attracted to the primary electromagnetic component 300 and the secondary electromagnetic component 610. On the contrary, a state when the movable magnetic core 450 is not attracted to the primary electromagnetic component 300 and the secondary electromagnetic component 610 is already shown in FIG. 25.

Figure 27:
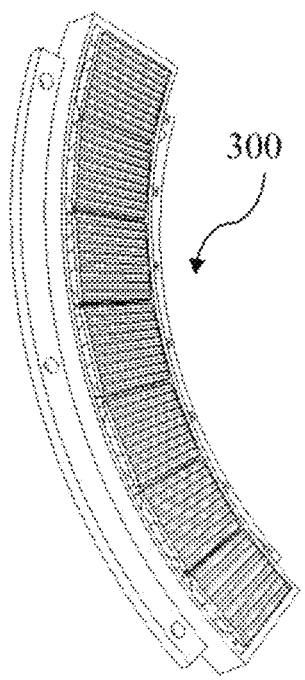
FIG. 27 and FIG. 28 both illustrate the primary electromagnetic component in FIG. 23.
Figure 28:
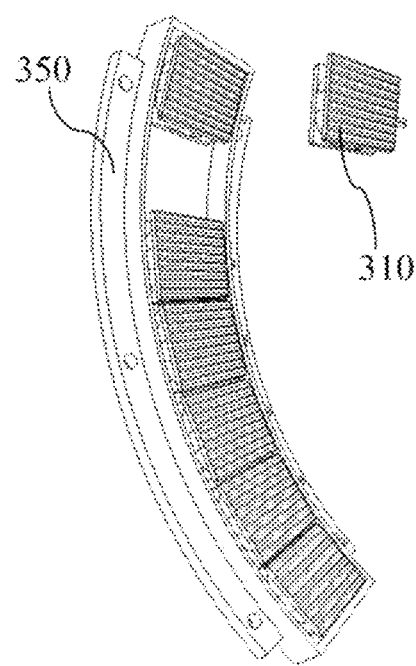

With reference to FIG. 27 and FIG. 28, FIG. 27 and FIG. 28 both illustrate the primary electromagnetic component 300 in FIG. 23. FIG. 28 further schematically illustrates a mounting mode of the electromagnetic units 310 in FIG. 25. The primary electromagnetic component 300 includes a plurality of electromagnetic units 310 sequentially adjacent to each other. These electromagnetic units 310 are arranged on a supporting plate 350 along an arc trajectory, or arranged on an arc-shaped supporting plate 350. The supporting plate 350 may be fixed to the tilt supporting frame 20 by means of screws or other connection methods.

Figure 29:
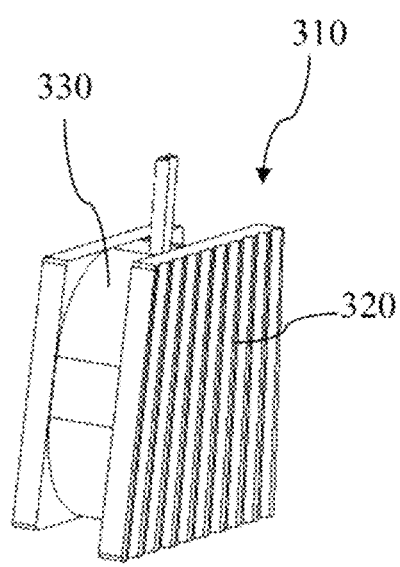
FIG. 29 illustrates an example structure of an electromagnetic unit in FIG. 27.
Figure 30:
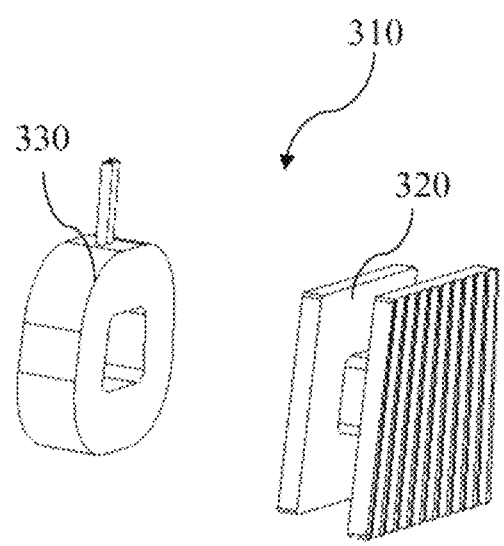
FIG. 30 illustrates an exploded structure of the electromagnetic unit in FIG. 29.

With reference to FIG. 29 and FIG. 30, FIG. 29 illustrates an example structure of the electromagnetic unit 310 in FIG. 28. FIG. 30 illustrates an exploded structure of the electromagnetic unit 310 in FIG. 29. The electromagnetic unit 310 includes an electromagnetic unit magnetic core 320. A cross-section of the electromagnetic unit magnetic core 320 forms an "H" shape including a shaft portion and end portions connected to two ends of the shaft portion. A coil component 330 is wound on the shaft portion of the electromagnetic unit magnetic core 320. The coil component 330 of any electromagnetic unit 310 may be used for receiving a current emitted by the power controller to control a working state of the electromagnetic unit 310. The coil components 330 of the plurality of electromagnetic units 310 may be connected in series or in parallel.

As shown in FIG. 23, the shielding part 800 may be disposed outside the engaging part 400 and used for shielding the fixing part 600 and at least part of the engaging part 400.

In the aforementioned embodiments of the present invention, a locking part is disposed on a tilt supporting frame that is tiltable, an engaging part is disposed on a relatively fixed bottom supporting frame, and the locking part is disposed according to a tilt trajectory of the tilt supporting frame so as to engage the engaging part disposed on the bottom supporting frame at any position within a tilting range, thereby firmly locking the tilt supporting frame, preventing a rotating part thereon from producing large vibration during high-speed rotation, and improving image quality of medical imaging.

Additionally, locking and unlocking of the tilt supporting frame may be implemented by means of clamping or releasing between a locking tongue and a slot, or the locking and unlocking may be implemented by means of attraction or releasing between electromagnetic components and a movable magnetic core, so that the tilt supporting frame can be reliably locked. Furthermore, manufacturing, mounting, and maintenance costs would be lowered.

Moreover, during locking, the locked state can be made stable by means of a fixing part. The fixing part additionally has desirable tolerance and the fixing part can attract the magnetic core by means of the same driving system, thereby facilitating product design.

Some exemplary embodiments have been described above. However, it should be understood that various modifications can be made by one skilled in the art. For example, if the described techniques are performed in a different order and/or if the components of the described system, architecture, system, or circuit are combined in other manners and/or replaced or supplemented with additional components or equivalents thereof, a suitable result can be achieved. Accordingly, other implementations still fall within the protection scope of the claims.

The invention claimed is:

1. A gantry for an imaging system, the gantry comprising:
   a bottom supporting frame and a tilt supporting frame that are connected to each other, wherein the tilt supporting frame is tiltable relative to the bottom supporting frame; and
   a locking mechanism connected between the bottom supporting frame and the tilt supporting frame;

wherein the locking mechanism comprises:
- a locking component disposed on the tilt supporting frame according to a tilt trajectory of the tilt supporting frame;
- an engaging component disposed on the bottom supporting frame, wherein the engaging component is used for engaging the locking component and locking the tilt supporting frame relative to the bottom supporting frame when moved from an initial unlocked position to a locked position, or used for unlocking the tilt supporting frame when returning from the locked position to the initial unlocked position; and
- a driving component used for driving the engaging component to the locked position or return to the initial unlocked position;
- wherein the locking component comprises a body and a slot extending into an arc shape formed on the body; and
- wherein the engaging component comprises a locking tongue capable of rotating from the initial unlocked position to the locked position to abut against at least one inner wall of the slot.

\* \* \* \* \*